(12) United States Patent
   Wu

(10) Patent No.: US 10,619,136 B2
(45) Date of Patent: *Apr. 14, 2020

(54) REDUCING IMMUNE TOLERANCE INDUCED BY PD-L1

(71) Applicant: Innovative Cellular Therapeutics CO., LTD., Shanghai (CN)

(72) Inventor: Zhao Wu, Shanghai (CN)

(73) Assignee: Innovative Cellular Therapeutics Co., Ltd., Shanghai (CN)

(*) Notice: Subject to any disclaimer, the term of this patent is extended or adjusted under 35 U.S.C. 154(b) by 392 days.

This patent is subject to a terminal disclaimer.

(21) Appl. No.: 15/373,012

(22) Filed: Dec. 8, 2016

(65) Prior Publication Data

US 2017/0096638 A1   Apr. 6, 2017

Related U.S. Application Data

(63) Continuation of application No. 15/093,643, filed on Apr. 7, 2016, now Pat. No. 9,572,837, which is a continuation of application No. PCT/CN2016/075061, filed on Mar. 1, 2016.

(60) Provisional application No. 62/126,804, filed on Mar. 2, 2015.

(51) Int. Cl.
   *C07K 16/30*     (2006.01)
   *C07K 14/705*    (2006.01)
   *C12N 5/0783*    (2010.01)
   *C07K 16/28*     (2006.01)
   *C07K 14/725*    (2006.01)
   *A61K 35/17*     (2015.01)
   *A61K 39/00*     (2006.01)

(52) U.S. Cl.
   CPC ............ *C12N 5/0636* (2013.01); *A61K 35/17* (2013.01); *A61K 39/0011* (2013.01); *C07K 14/7051* (2013.01); *C07K 14/70503* (2013.01); *C07K 14/70521* (2013.01); *C07K 16/2803* (2013.01); *C07K 16/30* (2013.01); *C12N 5/0638* (2013.01); *A61K 2039/5156* (2013.01); *A61K 2039/5158* (2013.01); *C07K 2319/00* (2013.01); *C07K 2319/02* (2013.01); *C07K 2319/03* (2013.01); *C12N 2510/02* (2013.01)

(58) Field of Classification Search
   None
   See application file for complete search history.

(56) References Cited

U.S. PATENT DOCUMENTS

| | | | |
|---|---|---|---|
| 6,120,766 A | 9/2000 | Hale et al. | |
| 8,906,682 B2 | 12/2014 | June et al. | |
| 8,911,993 B2 | 12/2014 | June et al. | |
| 8,916,381 B1 | 12/2014 | June et al. | |
| 8,975,071 B1 | 3/2015 | June et al. | |
| 9,101,584 B2 | 8/2015 | June et al. | |
| 9,102,760 B2 | 8/2015 | June et al. | |
| 9,102,761 B2 | 8/2015 | June et al. | |
| 9,572,837 B2 | 2/2017 | Wu | |
| 2014/0120622 A1 | 5/2014 | Gregory et al. | |
| 2014/0219975 A1 | 8/2014 | June et al. | |
| 2014/0302070 A1 | 10/2014 | Chen et al. | |
| 2016/0039903 A1 | 2/2016 | Ring et al. | |
| 2019/0316086 A1 | 10/2019 | Wu | |

FOREIGN PATENT DOCUMENTS

| | | |
|---|---|---|
| WO | WO2003022875 A2 | 3/2003 |
| WO | WO2013019615 A2 | 2/2013 |
| WO | WO2013176915 A1 | 11/2013 |
| WO | WO2014059173 A2 | 4/2014 |
| WO | WO2014145252 A2 | 9/2014 |
| WO | WO2014182066 A2 | 11/2014 |
| WO | WO2016022994 A2 | 2/2016 |

OTHER PUBLICATIONS

Boussiotis, V., et al., "Biochemical signaling of PD-1 on T cells and its functional implications," 2014, Cancer J ., 20(4):265-271.
European Search Report and Written Opinion dated Apr. 7, 2017 in European Application No. 16717825.0, a corresponding foreign application of U.S. Appl. No. 15/093,643, 8 pages.
Jensen, M., et al., "Design and implementation of adoptive therapy with chimeric antigen receptor-modified T cells," 2014, Immunological Reviews, 257:127-144.
John, L., et al., "Anti-PD-1 antibody therapy potently enhances the eradication of established tumors by gene-modified T cells," Oct. 2013, Clinical Cancer Research, 19(20): 5636-5646.
John, L., et al., "Blockade of PD-1 immunosuppression boosts CAR T-cell therapy," Oct. 2013, OncoImmunology, 2(10), e26286-1 to e26286-3.
PDCD1 homo isoform—Protein-NCBI, downloaded Aug. 26, 2016, from Http://www.ncbi.nlm.nih.gov/protein/?term=pdcd1+homo+isoform, 1 page.
Riley, J., et al., "PD-1 signaling in primary T cells," May 2009, Immunol Rev., 229(1):114-125.
Shi, H., et al., "Chimeric antigen receptor for adoptive immunotherapy of cancer: latest research and future prospects," 2014, Molecular Cancer, 13:219-226.
Ankri et al., "Human T cells engineered to express a programmed death 1/28 costimulatory retargeting molecule display enhanced antitumor activity," Sep. 2013. J Immunol, 191:4121-4129.
European Communication under Rule 114(2) Re: 3rd Party Observation mailed Feb. 5, 2019 in European patent application No. 16717825.0, a foreign corresponding application to U.S. Appl. No. 15/093,643, 4 pages.

(Continued)

*Primary Examiner* — Sharon X Wen
(74) *Attorney, Agent, or Firm* — Lee & Hayes, P.C.

(57) ABSTRACT

The present disclosure relates to compositions and methods for reducing immune tolerance associated with CAR T cell therapy. Embodiments of the present disclosure include isolated nucleic acid sequence comprising a nucleic acid sequence that encodes modified programmed cell death protein 1 (PD-1) and a nucleic acid sequence that encodes chimeric antigen receptor (CAR).

27 Claims, 11 Drawing Sheets
Specification includes a Sequence Listing.

(56) References Cited

OTHER PUBLICATIONS

Kalos et al., "T cells with chimeric antigen receptors have potent antitumor effects and can establish memory in patients with advanced leukemia," Aug. 2011. NIH Public Access Author Manuscript, Sci Transl Med., 3(95): 95ra73.

Locus XM_006712573 749 bp mRNA linear, "*Homo sapiens* programmed cell death 1 (PDCD1), transcript, variant X1, mRNA." Feb. 3, 2014. Version: XM_006712573.1, 3 pages.

European Communication under Rule 71(3) Re: European Examiner's comments to 3rd Party Observations mailed Apr. 3, 2019 in European patent application No. 16717825.0, a foreign corresponding application to U.S. Appl. No. 15/093,643, 1 page.

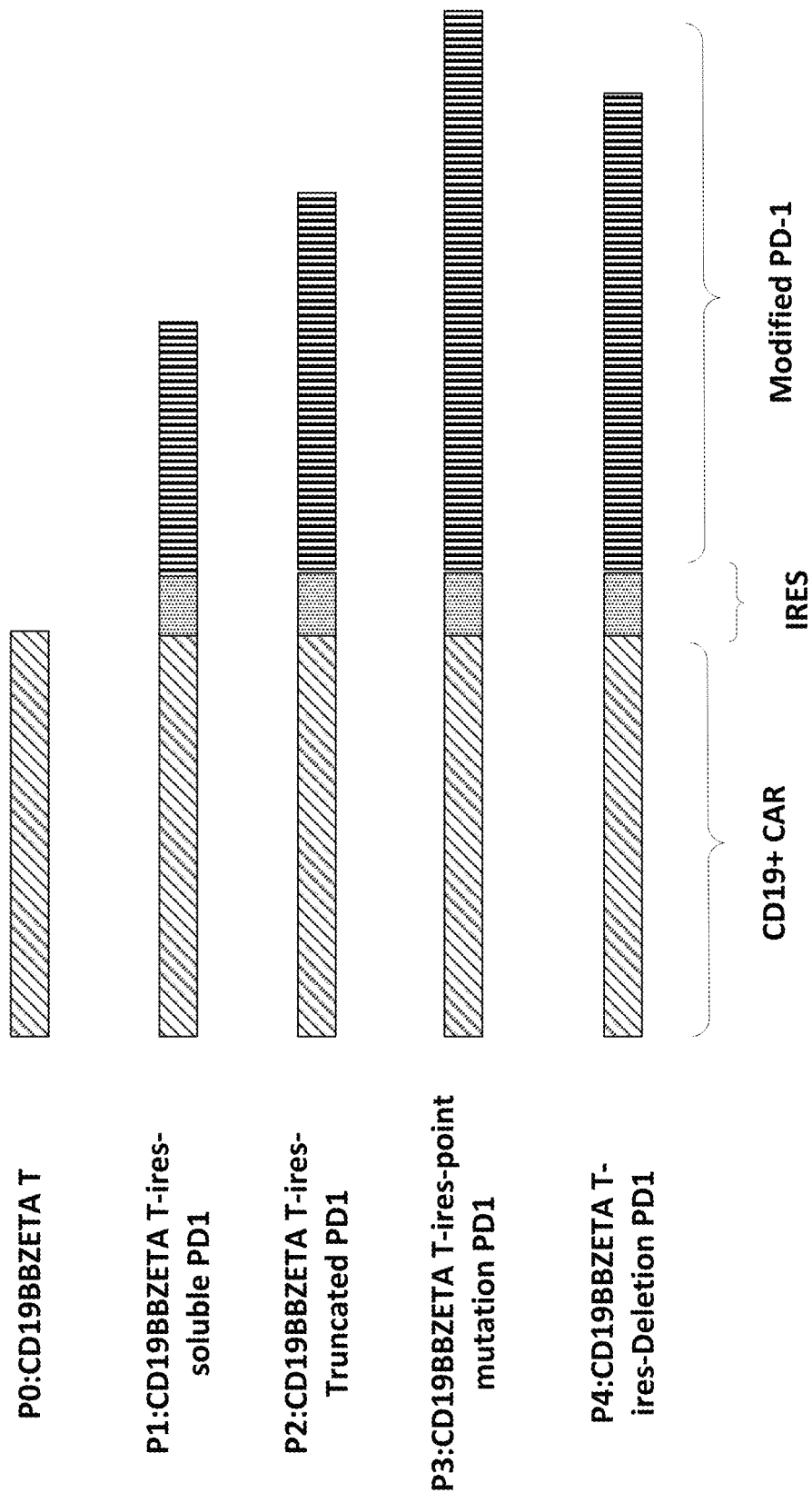

SEQUENCE LISTING

<160> NUMBER OF SEQ ID NOS: 16

<210> SEQ ID NO 1
<211> LENGTH: 1339
<212> TYPE: DNA
<213> ORGANISM: Artificial Sequence
<220> FEATURE:
<223> OTHER INFORMATION: Synthesized

<400> SEQUENCE: 1

| | | | | | |
|---|---|---|---|---|---|
| atggccttac | cagtgaccgc | cttgctcctg | ccgctggcct | tgctgctcca | cgccgccagg | 60 |
| ccggacatcc | agatgacaca | gactacatcc | tccctgtctg | cctctctggg | agacagagtc | 120 |
| accatcagtt | gcagggcaag | tcaggacatt | agtaaatatt | taaattggta | tcagcagaaa | 180 |
| ccagatggaa | ctgttaaact | cctgatctac | catacatcaa | gattacactc | aggagtccca | 240 |
| tcaaggttca | gtggcagtgg | gtctgggaca | gattattctc | tcaccattag | caacctggag | 300 |
| caagaagata | ttgccactta | cttttgccaa | cagggtaata | cgcttccgta | cacgttcgga | 360 |
| ggggggacca | agctggagat | cacaggtggc | ggtggctcgg | gcggtggtgg | gtcgggtggc | 420 |
| ggcggatctg | aggtgaaact | gcaggagtca | ggacctggcc | tggtggcgcc | ctcacagagc | 480 |
| ctgtccgtca | catgcactgt | ctcagggggtc | tcattacccg | actatggtgt | aagctggatt | 540 |
| cgccagcctc | cacgaaaggg | tctggagtgg | ctgggagtaa | tatggggtag | tgaaaccaca | 600 |
| tactataatt | cagctctcaa | atccagactg | accatcatca | aggacaactc | caagagccaa | 660 |
| gttttcttaa | aaatgaacag | tctgcaaact | gatgacacag | ccatttacta | ctgtgccaaa | 720 |
| cattattact | acggtggtag | ctatgctatg | gactactggg | gccaaggaac | ctcagtcacc | 780 |
| gtctcctcaa | ccacgacgcc | agcgccgcga | ccaccaacac | cggcgcccac | catcgcgtcg | 840 |
| cagcccctgt | ccctgcgccc | agaggcgtgc | cggccagcgg | cggggggcgc | agtgcacacg | 900 |
| agggggctgg | acttcgcctg | tgatatctac | atctgggcgc | ccttggccgg | acttgtgggg | 960 |
| gtccttctcc | tgtcactggt | tatcacccttt | tactgcaaac | ggggcagaaa | gaaactcctg | 1020 |
| tatatattca | acaaccatt | tatgagacca | gtacaaacta | ctcaagagga | agatggctgt | 1080 |
| agctgccgat | ttcagaagaa | agaagaagga | ggatgtgaac | tgagagtgaa | gttcagcagg | 1140 |
| agcgcagacg | cccccgcgta | caagcagggc | cagaaccagc | tctataacga | gctcaatcta | 1200 |
| ggacgaagag | aggagtacga | tgttttggac | aagagacgtg | gccgggaccc | tgagatgggg | 1260 |
| ggaaagccga | gaaggaagaa | ccctcaggaa | ggcctgtaca | atgaactgca | gaaagataag | 1320 |
| atggcggagg | cctacagtg | | | | | 1339 |

<210> SEQ ID NO 2
<211> LENGTH: 1152
<212> TYPE: DNA
<213> ORGANISM: Artificial Sequence
<220> FEATURE:
<223> OTHER INFORMATION: Synthesized

<400> SEQUENCE: 2

| | | | | | |
|---|---|---|---|---|---|
| cctctccctc | cccccccct | aacgttactg | gccgaagccg | cttggaataa | ggccggtgtg | 60 |
| cgtttgtcta | tatgttattt | tccaccatat | tgccgtcttt | tggcaatgtg | agggcccgga | 120 |
| aacctggccc | tgtcttcttg | acgagcattc | ctagggggtct | ttcccctctc | gccaaaggaa | 180 |
| tgcaaggtct | gttgaatgtc | gtgaaggaag | cagttcctct | ggaagcttct | tgaagacaaa | 240 |
| caacgtctgt | agcgacccctt | tgcaggcagc | ggaacccccc | acctggcgac | aggtgcctct | 300 |
| gcggccaaaa | gccacgtgta | taagatacac | ctgcaaaggc | ggcacaaccc | cagtgccacg | 360 |

```
ttgtgagttg datagttgtg gaaagagtca aatggctctc ctcaagcgta ttcaacaagg      420
ggctgaagga tgcccagaag gtaccccatt gtatgggatc tgatctgggg cctcggtaca      480
catgctttac atgtgtttag tcgaggttaa aaaaacgtct aggcccccg aaccacgggg       540 acgtggtttt cctttgaaaa acacgatgat aatatggcca caaccatgca gatcccacag      600
gcgccctggc cagtcgtctg ggcggtgcta caactgggct ggcggccagg atggttctta      660
gactccccag acaggccctg gaaccccccc accttctccc cagccctgct cgtggtgacc      720 gaagggggaca acgccacctt cacctgcagc ttctccaaca catcggagag cttcgtgcta     780
aactggtacc gcatgagccc cagcaaccag acggacaagc tggccgcctt ccccgaggac      840
cgcagccagc ccggccagga ctgccgcttc cgtgtcacac aactgcccaa cgggcgtgac      900
ttccacatga gcgtggtcag ggcccggcgc aatgacagcg gcacctacct ctgtggggcc      960
atctccctgg cccccaaggc gcagatcaaa gagagcctgc gggcagagct cagggtgaca    1020
gagagaaggg cagaagtgcc cacagcccac cccagcccct cacccaggcc agccggccag    1080
ttccaaaccc tggtgggtaa tattctgaat gtgtccatta aaatatgtct aacactgtcc    1140
cctagcacct aa                                                         1152

<210> SEQ ID NO 3
<211> LENGTH: 1188
<212> TYPE: DNA
<213> ORGANISM: Artificial Sequence
<220> FEATURE:
<223> OTHER INFORMATION: Synthesized

<400> SEQUENCE: 3
cctctccctc ccccccccct aacgttactg gccgaagccg cttggaataa ggccggtgtg       60
cgtttgtcta tatgttattt tccaccatat tgccgtcttt tggcaatgtg agggcccgga     120
aacctggccc tgtcttcttg acgagcattc ctaggggtct ttcccctctc gccaaaggaa     180
tgcaaggtct gttgaatgtc gtgaaggaag cagttcctct ggaagcttct tgaagacaaa    240
caacgtctgt agcgaccctt gcaggcagcg gaaccccccc acctggcgac aggtgcctct    300
gcggccaaaa gccacgtgta taagatacac ctgcaaaggc ggcacaaccc cagtgccacg    360
ttgtgagttg datagttgtg gaaagagtca aatggctctc ctcaagcgta ttcaacaagg    420
ggctgaagga tgcccagaag gtaccccatt gtatgggatc tgatctgggg cctcggtaca    480
catgctttac atgtgtttag tcgaggttaa aaaaacgtct aggcccccg aaccacgggg     540 acgtggtttt cctttgaaaa acacgatgat aatatggcca caaccatgca gatcccacag    600
gcgccctggc cagtcgtctg ggcggtgcta caactgggct ggcggccagg atggttctta    660
gactccccag acaggccctg gaaccccccc accttctccc cagccctgct cgtggtgacc    720 gaagggggaca acgccacctt cacctgcagc ttctccaaca catcggagag cttcgtgcta   780
aactggtacc gcatgagccc cagcaaccag acggacaagc tggccgcctt ccccgaggac    840
cgcagccagc ccggccagga ctgccgcttc cgtgtcacac aactgcccaa cgggcgtgac    900
ttccacatga gcgtggtcag ggcccggcgc aatgacagcg gcacctacct ctgtggggcc    960
atctccctgg cccccaaggc gcagatcaaa gagagcctgc gggcagagct cagggtgaca   1020
gagagaaggg cagaagtgcc cacagcccac cccagcccct cacccaggcc agccggccag   1080
ttccaaaccc tggtggttgg tgtcgtgggc ggcctgctgg gcagcctggt gctgctagtc   1140
tgggtcctgg ccgtcatctg ctcccgggcc gcacgaggga caatataa                1188
```

<210> SEQ ID NO 4
<211> LENGTH: 1452
<212> TYPE: DNA
<213> ORGANISM: Artificial Sequence
<220> FEATURE:
<223> OTHER INFORMATION: Synthesized

<400> SEQUENCE: 4

| | | | | | |
|---|---|---|---|---|---|
| cctctccctc | cccccccct | aacgttactg | gccgaagccg | cttggaataa | ggccggtgtg | 60 |
| cgtttgtcta | tatgttattt | tccaccatat | tgccgtcttt | tggcaatgtg | agggcccgga | 120 |
| aacctggccc | tgtcttcttg | acgagcattc | ctagggtct | ttccctctc | gccaaggaa | 180 |
| tgcaaggtct | gttgaatgtc | gtgaaggaag | cagttcctct | ggaagcttct | tgaagacaaa | 240 |
| caacgtctgt | agcgacccttt | tgcaggcagc | ggaaccccc | acctggcgac | aggtgcctct | 300 |
| gcggccaaaa | gccacgtgta | taagatacac | ctgcaaaggc | ggcacaaccc | cagtgccacg | 360 |
| ttgtgagttg | gatagttgtg | gaaagagtca | aatggctctc | ctcaagcgta | ttcaacaagg | 420 |
| ggctgaagga | tgcccagaag | gtaccccatt | gtatgggatc | tgatctgggg | cctcggtaca | 480 |
| catgctttac | atgtgtttag | tcgaggttaa | aaaaacgtct | aggccccccg | aaccacgggg | 540 |
| acgtggtttt | cctttgaaaa | acacgatgat | aatatgccca | caaccatgca | gatcccacag | 600 |
| gcgccctggc | cagtcgtctg | ggcggtgcta | caactgggct | ggcggccagg | atggttctta | 660 |
| gactccccag | acaggccctg | gaaccccccc | accttctccc | cagccctgct | cgtggtgacc | 720 |
| gaaggggaca | cgccaccctt | cacctgcagc | ttctccaaca | catcggagag | cttcgtgcta | 780 |
| aactggtacc | gcatgagccc | cagcaaccag | acggacaagc | tggccgcctt | ccccgaggac | 840 |
| cgcagccagc | ccggccagga | ctgccgcttc | cgtgtcacac | aactgcccaa | cgggcgtgac | 900 |
| ttccacatga | gcgtggtcag | ggcccggcgc | aatgacagcg | gcacctacct | ctgtggggcc | 960 |
| atctccctgg | ccccaaggc | gcagatcaaa | gagagcctgc | gggcagagct | cagggtgaca | 1020 |
| gagagaaggg | cagaagtgcc | cacagcccac | cccagcccct | cacccaggcc | agccggccag | 1080 |
| ttccaaaccc | tggtggttgg | tgtcgtgggc | ggcctgctgg | gcagcctggt | gctgctagtc | 1140 |
| tgggtcctgg | ccgtcatctg | ctcccgggcc | gcacgaggga | caataggagc | caggcgcacc | 1200 |
| ggccagcccc | tgaaggagga | cccctcagcc | gtgcctgtgt | tctctgtgga | cgccggggag | 1260 |
| ctggatttcc | agtggcgaga | gaagacccccg | gagcccccg | tgccctgtgt | ccctgagcag | 1320 |
| acggaggccg | ccaccattgt | ctttcctagc | ggaatgggca | cctcatcccc | cgcccgcagg | 1380 |
| ggctcagctg | acggccctcg | gagtgcccag | ccactgaggc | ctgaggatgg | acactgctct | 1440 |
| tggcccctct | ga | | | | | 1452 |

<210> SEQ ID NO 5
<211> LENGTH: 1212
<212> TYPE: DNA
<213> ORGANISM: Artificial Sequence
<220> FEATURE:
<223> OTHER INFORMATION: Synthesized

<400> SEQUENCE: 5

| | | | | | |
|---|---|---|---|---|---|
| cctctccctc | cccccccct | aacgttactg | gccgaagccg | cttggaataa | ggccggtgtg | 60 |
| cgtttgtcta | tatgttattt | tccaccatat | tgccgtcttt | tggcaatgtg | agggcccgga | 120 |
| aacctggccc | tgtcttcttg | acgagcattc | ctagggtct | ttccctctc | gccaaggaa | 180 |
| tgcaaggtct | gttgaatgtc | gtgaaggaag | cagttcctct | ggaagcttct | tgaagacaaa | 240 |
| caacgtctgt | agcgacccttt | tgcaggcagc | ggaaccccc | acctggcgac | aggtgcctct | 300 |

```
gcggccaaaa gccacgtgta taagatacac ctgcaaaggc ggcacaaccc cagtgccacg      360
ttgtgagttg gatagttgtg gaaagagtca aatggctctc ctcaagcgta ttcaacaagg      420
ggctgaagga tgcccagaag gtaccccatt gtatgggatc tgatctgggg cctcggtaca      480
catgctttac atgtgtttag tcgaggttaa aaaaacgtct aggccccccg aaccacgggg      540
acgtggtttt cctttgaaaa acacgatgat aatatggcca caaccatgca gatcccacag      600
gcgccctggc cagtcgtctg gcggtgcta caactgggct ggcggccagg atggttctta       660
gactccccag acaggccctg aaccccccc accttctccc cagccctgct cgtggtgacc       720 gaagggaca cgccacctt cacctgcagc ttctccaaca catcggagag cttcgtgcta        780
aactggtacc gcatgagccc cagcaaccag acggacaagc tggccgcctt ccccgaggac      840
cgcagccagc ccggccagga ctgccgcttc cgtgtcacac aactgcccaa cgggcgtgac      900
ttccacatga gcgtggtcag ggcccggcgc aatgacagcg gcacctacct ctgtggggcc      960
atctccctgg cccccaaggc gcagatcaaa gagagcctgc gggcagagct cagggtgaca     1020
gagagaaggg cagaagtgcc cacagcccac cccagcccct cacccaggcc agccggccag     1080
ttccaaaccc tggtggttgg tgtcgtgggc ggcctgctgg cagcctggt gctgctagtc      1140 tgggtcctgg ccgtcatctg ctcccgggcc gcacgaggga caatagatgg acactgctct     1200 tggccccctct aa                                                        1212

<210> SEQ ID NO 6
<211> LENGTH: 585
<212> TYPE: DNA
<213> ORGANISM: Artificial Sequence
<220> FEATURE:
<223> OTHER INFORMATION: Synthesized

<400> SEQUENCE: 6
cctctccctc ccccccccct aacgttactg gccgaagccg cttggaataa ggccggtgtg       60
cgtttgtcta tatgttattt tccaccatat tgccgtcttt tggcaatgtg agggcccgga      120
aacctggccc tgtcttcttg acgagcattc ctaggggtct ttcccctctc gccaaaggaa      180
tgcaaggtct gttgaatgtc gtgaaggaag cagttcctct ggaagcttct tgaagacaaa      240
caacgtctgt agcgaccctt gcaggcagc ggaaccccccc acctggcgac aggtgcctct     300
gcggccaaaa gccacgtgta taagatacac ctgcaaaggc ggcacaaccc cagtgccacg      360
ttgtgagttg gatagttgtg gaaagagtca aatggctctc ctcaagcgta ttcaacaagg      420
ggctgaagga tgcccagaag gtaccccatt gtatgggatc tgatctgggg cctcggtaca      480
catgctttac atgtgtttag tcgaggttaa aaaaacgtct aggccccccg aaccacgggg      540
acgtggtttt cctttgaaaa acacgatgat aatatggcca caacc                     585

<210> SEQ ID NO 7
<211> LENGTH: 2178
<212> TYPE: DNA
<213> ORGANISM: Artificial Sequence
<220> FEATURE:
<223> OTHER INFORMATION: Synthesized

<400> SEQUENCE: 7
atgaggatat ttgctgtctt tatattcatg acctactggc atttgctgaa cgcatttact       60
gtcacggttc ccaaggacct atatgtggta gagtatggta gcaatatgac aattgaatgc      120
aaattcccag tagaaaaaca attagacctg gctgcactaa ttgtctattg ggaaatggag      180
```

```
gataagaaca ttattcaatt tgtgcatgga gaggaagacc tgaaggttca gcatagtagc    240
tacagacaga gggcccggct gttgaaggac cagctctccc tgggaaatgc tgcacttcag    300
atcacagatg tgaaattgca ggatgcaggg gtgtaccgct gcatgatcag ctatggtggt    360
gccgactaca agcgaattac tgtgaaagtc aatgccccat acaacaaaat caaccaaaga    420
attttggttg tggatccagt cacctctgaa catgaactga catgtcaggc tgagggctac    480
cccaaggccg aagtcatctg gacaagcagt gaccatcaag tcctgagtgg taagaccacc    540
accaccaatt ccaagagaga ggagaagctt ttcaatgtga ccagcacact gagaatcaac    600
acaacaacta atgagatttt ctactgcact tttaggagat tagatcctga ggaaaaccat    660
acagctgaat tggtcatccc agaactacct ctggcacatc ctccaaatga aaggactcac    720
ttggtaattc tgggagccat cttattatgc cttggtgtag cactgacatt catcttccgt    780
ttaagaaaag ggagaatgat ggatgtgaaa aaatgtggca tccaagatac aaactcaaag    840
aagcaaagtg atacacattt ggaggagacg taacctctcc ctccccccc cctaacgtta    900 ctggccgaag ccgcttggaa taaggccggt gtgcgtttgt ctatatgtta ttttccacca    960
tattgccgtc ttttggcaat gtgagggccc ggaaacctgg ccctgtcttc ttgacgagca   1020
ttcctagggg tctttcccct ctcgccaaag gaatgcaagg tctgttgaat gtcgtgaagg   1080
aagcagttcc tctggaagct tcttgaagac aaacaacgtc tgtagcgacc ctttgcaggc   1140
agcggaaccc cccacctggc gacaggtgcc tctgcggcca aaagccacgt gtataagata   1200
cacctgcaaa ggcggcacaa ccccagtgcc acgttgtgag ttggatagtt gtggaaagag   1260
tcaaatggct ctcctcaagc gtattcaaca aggggctgaa ggatgcccag aaggtaccc   1320 attgtatggg atctgatctg gggcctcggt acacatgctt tacatgtgtt tagtcgaggt   1380
taaaaaaacg tctaggcccc ccgaaccacg ggacgtggt tttcctttga aaaacacgat    1440
gataatatgg ccacaaccat ggtgagcaag ggcgaggagc tgttcaccgg ggtggtgccc   1500
atcctggtcg agctggacgg cgacgtaaac ggccacaagt tcagcgtgtc cggcgagggc   1560
gagggcgatg ccacctacgg caagctgacc ctgaagttca tctgcaccac cggcaagctg   1620
cccgtgccct ggcccaccct cgtgaccacc ctgacctacg gcgtgcagtg cttcagccgc   1680
taccccgacc acatgaagca gcacgacttc ttcaagtccg ccatgcccga aggctacgtc   1740
caggagcgca ccatcttctt caaggacgac ggcaactaca agacccgcgc cgaggtgaag   1800
ttcgagggcg acaccctggt gaaccgcatc gagctgaagg gcatcgactt caaggaggac   1860
ggcaacatcc tggggcacaa gctggagtac aactacaaca gccacaacgt ctatatcatg   1920
gccgacaagc agaagaacgg catcaaggtg aacttcaaga tccgccacaa catcgaggac   1980
ggcagcgtgc agctcgccga ccactaccag cagaacaccc ccatcggcga cggccccgtg   2040
ctgctgcccg acaaccacta cctgagcacc cagtccgccc tgagcaaaga ccccaacgag   2100
aagcgcgatc acatggtcct gctggagttc gtgaccgccg ccgggatcac tctcggcatg   2160
gacgagctgt acaagtaa                                                 2178
```

<210> SEQ ID NO 8
<211> LENGTH: 20
<212> TYPE: PRT
<213> ORGANISM: Artificial Sequence
<220> FEATURE:
<223> OTHER INFORMATION: Synthesized

<400> SEQUENCE: 8

Met Gln Ile Pro Gln Ala Pro Trp Pro Val Val Trp Ala Val Leu Gln

```
1               5                   10                  15

Leu Gly Trp Arg
            20

<210> SEQ ID NO 9
<211> LENGTH: 150
<212> TYPE: PRT
<213> ORGANISM: Artificial Sequence
<220> FEATURE:
<223> OTHER INFORMATION: Synthesized

<400> SEQUENCE: 9

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 10
<211> LENGTH: 21
<212> TYPE: PRT
<213> ORGANISM: Artificial Sequence
<220> FEATURE:
<223> OTHER INFORMATION: Synthesized

<400> SEQUENCE: 10

Val Gly Val Val Gly Gly Leu Leu Gly Ser Leu Val Leu Leu Val Trp
1               5                   10                  15

Val Leu Ala Val Ile
            20

<210> SEQ ID NO 11
<211> LENGTH: 18
<212> TYPE: PRT
<213> ORGANISM: Artificial Sequence
<220> FEATURE:
<223> OTHER INFORMATION: Synthesized

<400> SEQUENCE: 11

Gly Asn Ile Leu Asn Val Ser Ile Lys Ile Cys Leu Thr Leu Ser Pro
1               5                   10                  15

Ser Thr

<210> SEQ ID NO 12
<211> LENGTH: 9
```

```
<212> TYPE: PRT
<213> ORGANISM: Artificial Sequence
<220> FEATURE:
<223> OTHER INFORMATION: Synthesized

<400> SEQUENCE: 12

Cys Ser Arg Ala Ala Arg Gly Thr Ile
1               5

<210> SEQ ID NO 13
<211> LENGTH: 97
<212> TYPE: PRT
<213> ORGANISM: Artificial Sequence
<220> FEATURE:
<223> OTHER INFORMATION: Synthesized

<400> SEQUENCE: 13

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Ala
                20                  25                  30

Gly Glu Leu Asp Phe Gln Trp Arg Glu Lys Thr Pro Glu Pro Pro Val
            35                  40                  45

Pro Cys Val Pro Glu Gln Thr Glu Ala Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu

<210> SEQ ID NO 14
<211> LENGTH: 17
<212> TYPE: PRT
<213> ORGANISM: Artificial Sequence
<220> FEATURE:
<223> OTHER INFORMATION: Synthesized

<400> SEQUENCE: 14

Cys Ser Arg Ala Ala Arg Gly Thr Ile Asp Gly His Cys Ser Trp Pro
1               5                   10                  15

Leu

<210> SEQ ID NO 15
<211> LENGTH: 88
<212> TYPE: PRT
<213> ORGANISM: Artificial Sequence
<220> FEATURE:
<223> OTHER INFORMATION: Synthesized

<400> SEQUENCE: 15

Gly Ala Arg Arg Thr Gly Gln Pro Leu Lys Glu Asp Pro Ser Ala Val
1               5                   10                  15

Pro Val Phe Ser Val Asp Tyr Gly Glu Leu Asp Phe Gln Trp Arg Glu
                20                  25                  30

Lys Thr Pro Glu Pro Pro Val Pro Cys Val Pro Glu Gln Thr Glu Tyr
                35                  40                  45

Ala Thr Ile Val Phe Pro Ser Gly Met Gly Thr Ser Ser Pro Ala Arg
        50                  55                  60

Arg Gly Ser Ala Asp Gly Pro Arg Ser Ala Gln Pro Leu Arg Pro Glu
65                  70                  75                  80
```

```
Asp Gly His Cys Ser Trp Pro Leu
                85

<210> SEQ ID NO 16
<211> LENGTH: 80
<212> TYPE: PRT
<213> ORGANISM: Artificial Sequence
<220> FEATURE:
<223> OTHER INFORMATION: Synthesized

<400> SEQUENCE: 16

Gly Ala Arg Arg Thr Gly Gln Pro Leu Lys Glu Asp Pro Ser Ala Val
1               5                   10                  15

Pro Val Phe Ser Val Asp Tyr Gly Glu Leu Asp Phe Gln Trp Arg Glu
                20                  25                  30

Lys Thr Pro Glu Pro Pro Val Pro Cys Val Pro Glu Gln Thr Glu Tyr
            35                  40                  45

Ala Thr Ile Val Phe Pro Ser Gly Met Gly Thr Ser Ser Pro Ala Arg
        50                  55                  60

Arg Gly Ser Ala Asp Gly Pro Arg Ser Ala Gln Pro Leu Arg Pro Glu
65                  70                  75                  80
```

REDUCING IMMUNE TOLERANCE INDUCED BY PD-L1

CROSS REFERENCE TO RELATED PATENT APPLICATIONS

This application is a continuation application of U.S. patent application Ser. No. 15/093,643, filed Apr. 7, 2016, title "Reducing Immune Tolerance Induced by PH-L1," which claims priority to an International application number PCT/CN2016/075061, filed Mar. 1, 2016, title "Reducing Immune Tolerance Induced by PD-L1," which claims priority to U.S. Provisional Patent Application No. 62/126,804, filed on Mar. 2, 2015, entitled "Modified Cell and Uses thereof," which is hereby incorporated by reference in its entirety.

SEQUENCE LISTING

The Sequence Listing associated with this application is provided in text format in lieu of a paper copy and is hereby incorporated by reference into the specification. The name of the text file containing the Sequence Listing is SDS1.0005US Sequence_ST25.txt. The text file is about 19 KB and is submitted electronically via EFS-Web.

TECHNICAL FIELD

The present disclosure relates to modified cells and users, in particularly to compositions and methods for reducing immune tolerance associated with CART cell therapy.

BACKGROUND

T cell therapies have demonstrated efficacy and the therapeutic potential for treating cancers. However, their uses are limited by the presence of an immunosuppressive microenvironment. The immunosuppressive microenvironment includes immune tolerance induced by the interaction between programmed death-1 (PD-1) and PD-L1 ligand (PD-L1). PD-1 is a negative coregulatory receptor on T cells and antigen-presenting cells. The PD-L1 is expressed by several cell types (e.g., tumor cells and other tissue cells), and appears to be dynamically regulated by the immune microenvironment. Therefore, there is a need to address immune tolerance induced by the PD-L1 as to improve the efficacy of T cell therapies.

SUMMARY

Embodiments of the present disclosure relate to an isolated nucleic acid sequence comprising a nucleic acid sequence that encodes modified programmed cell death protein 1 (PD-1) and a nucleic acid sequence that encodes chimeric antigen receptor (CAR). In certain embodiments, the modified PD-1 and the CAR are expressed as gene products that are separate polypeptides.

In some embodiments, the CAR is specific for a tumor antigen that is present on a cancer cell, and wherein the cancer cell expresses PD-L1.

In some embodiments, the tumor antigen comprises HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor.

In some embodiments, the nucleic acid sequence that encodes the modified PD-1 comprises substitution or deletion of one or more nucleotides as compared to a nucleic acid sequence encoding an intracellular part of wild-type PD-1.

In some embodiments, the nucleic acid sequence that encodes the modified PD-1 comprises a deletion of multiple nucleotides as compared to a nucleic acid sequence encoding an intracellular part of wild-type PD-1. In certain embodiments, the modified PD-1 comprises the amino acid sequence of SEQ ID NO: 14.

In some embodiments, the nucleic acid sequence that encodes the modified PD-1 comprises a nucleic acid encoding a truncated PD-1 that does not include an intracellular domain. In certain embodiments, the nucleic acid sequence that encodes the modified PD-1 comprises the amino acid sequence of SEQ ID NO: 12.

In some embodiments, the modified PD-1 comprises one or more point mutations as compared to wild-type PD-1. In certain embodiments, the point mutation comprises one or two amino acid point mutations of phosphorylation sites of wild-type PD-1.

The embodiments further relate to an expression vector comprising the nucleic acid sequence as described above. In some embodiments, the expression vector is a viral vector selected from the group consisting of a retroviral vector, lentiviral vector, adenoviral vector, and an adeno-associated viral vector.

The embodiments further relate to a cell comprising the expression vector of the present disclosure. In some embodiments, the cell is selected from the group consisting of a T cell, NK cell, and an NKT cell.

The embodiments further relate to a pharmaceutical composition comprising an antitumor effective amount of a population of human T cells, wherein the human T cells of the population include human T-cells that comprise the isolated nucleic acid sequence as described above. In some embodiments, an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1.

The embodiments further relate to a method of treating cancer in a human patient, the method comprising administering to the human patient the pharmaceutical composition as described in the present disclosure.

The embodiments further relate to a cell engineered to express modified PD-1 and chimeric antigen receptors (CAR), wherein the modified PD-1 does not include a transmembrane part or an intracellular part of PD-1, or a combination thereof. In some embodiments, the cell expresses soluble PD-1 such as to disrupt PD-1 binding to PD-L-1. For example, the soluble PD-1 is not attached to a cell membrane of the cell.

The embodiments further relate to a method of treating and/or inhibiting cancer of a subject. The method includes administering to the subject a therapeutically effective amount of a soluble receptor including an extracellular domain of PD-1. In some embodiments, the soluble receptor binds a PD-L1 protein, and the soluble receptor disrupts PD-1 signaling of cancer cells and/or disrupts PD-1 binding to PD-L1. In certain embodiments, the isolated soluble receptor polypeptide includes the amino acid residues of SEQ ID NO:9.

The embodiments further related to modified cell including a receptor polypeptide, a cytoplasmic domain of the receptor polypeptide being truncated, the receptor polypeptide being at least one of a Programmed cell death protein 1 (PD-1) receptor polypeptide, cytotoxic T-lymphocyte-associated protein 4 (CTLA-4) receptor polypeptide, or B- and T-lymphocyte attenuator (BTLA) receptor.

The embodiments further relate to a method for treating a subject having a disease. The method includes administering a cell to the subject having the disease, wherein the cell is genetically modified to express a receptor polypeptide, a cytoplasmic domain of the receptor polypeptide being truncated, the receptor polypeptide being at least one of a Programmed cell death protein 1 (PD-1) receptor polypeptide, cytotoxic T-lymphocyte-associated protein 4 (CTLA-4) receptor polypeptide, or B- and T-lymphocyte attenuator (BTLA) receptor; and a chimeric antigen receptor (CAR) including an antigen recognition domain of a specific antibody and an intracellular domain or a modified or wild-type T cell receptor, the specific antibody binding to an antigen.

In some embodiments, the receptor polypeptide is the PD-1 receptor polypeptide, and wherein the cytoplasmic domain of the PD-1 receptor polypeptide contains an immunoreceptor tyrosine-based motif.

The embodiments further relate to modified cell including a reduced amount of one or more receptors as compared to a corresponding wild-type cell, the one or more receptors including at least one of a Programmed cell death protein 1 (PD-1), cytotoxic T-lymphocyte-associated protein 4 (CTLA-4), or B- and T-lymphocyte attenuator (BTLA).

The embodiments further relate to a method for treating a subject having a disease. The method includes administering a cell to the subject having the disease, wherein the cell is modified to express a reduced amount of one or more receptors as compared to a corresponding wild-type cell, the one or more receptors including at least one of a Programmed cell death protein 1 (PD-1), cytotoxic T-lymphocyte-associated protein 4 (CTLA-4), or B- and T-lymphocyte attenuator (BTLA).

In some embodiments, modified cell further includes a chimeric antigen receptor (CAR) including an antigen recognition domain of a specific antibody and an intracellular domain, or a modified or wild-type T cell receptor. In certain embodiments, the modified cell further includes a chimeric antigen receptor (CAR) including an antigen recognition domain of a specific antibody and an intracellular domain or a modified or wild-type T cell receptor, the specific antibody binding to an antigen.

In some embodiments, the modified cell has reduced expression of one or more genes associated with a biosynthesis pathway or transportation pathway of the one or more receptors as compared to the corresponding wild-type cell, or a combination thereof. In certain embodiments, the modified cell includes a disruption of the one or more genes. In certain embodiments, the modified cell includes a partial or a complete deletion of the one or more genes. In certain embodiments, the genetically modified cell replicate in vivo in the human patient.

In some embodiments, the modified cell from memory cells in the human patient. In these instances, the modified cells are administered intravenously to the human patient. In certain embodiments, the modified cells persist in the human patient. For example, the modified cell is an autologous T cell. For another example, the cell may include at least one of a B cell, a T cell, an NK cell, an embryonic cell, or a dendritic cell.

In some embodiments, the disease may include at least one of cancer, immune deficiencies, autoimmune disease, or obesity.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

FIG. 1 a schematic diagram illustrating DNA constructs of P0:CD19BBZETA, P1: CD19BBZETA-ires-soluble PD1, P2:CD19BBZETA-ires-Truncated PD1, P3: CD19BBZETA-ires-point mutation PD1, P4:CD19BBZETA-ires-Deletion PD1.

FIG. 2, including FIG. 2A shows expression of CAR on transduced 293T and K562 cells. FIG. 2B shows expression of modified PD-1 on transduced 293T and K562 cells.

FIG. 3, including FIG. 3A shows expression of CAR on transduced primary T cells. FIGS. 3B and 3C show expression of modified PD-1 on transduced primary T cells.

FIG. 4, including FIG. 4A show IFN-Gamma release by per $10^4$ T cells transduced with CAR and modified PD-1s at the E:T ratio of 10:1 of culturing with CD19+ for 24 hours. FIG. 4B demonstrates that CD19+ cells were killed by per $10^4$ T cells transduced with CAR and modified PD-1s at the E:T ratio of 10:1 of culturing for 24 hours.

FIG. 6, including FIG. 6A shows IFN-gamma release of per $10^4$ T cells transduced with CAR and modified PD-1s at the E:T ratio of 10:1 of culturing with CD19+ cells and CD19+/PD-L1+ cells for 24 hours. These results demonstrate that Inhibition of cytotoxicity induced by PD-L1 decreases on T cells transduced with CAR and modified PD-1.

FIG. 6B illustrates the loss of cytotoxicity induced by a PD-L1 decrease on T cells transduced with CAR and modified PD-1 as compared to T cells transduced with CAR alone.

DETAILED DESCRIPTION

Overview

Figure 2A:
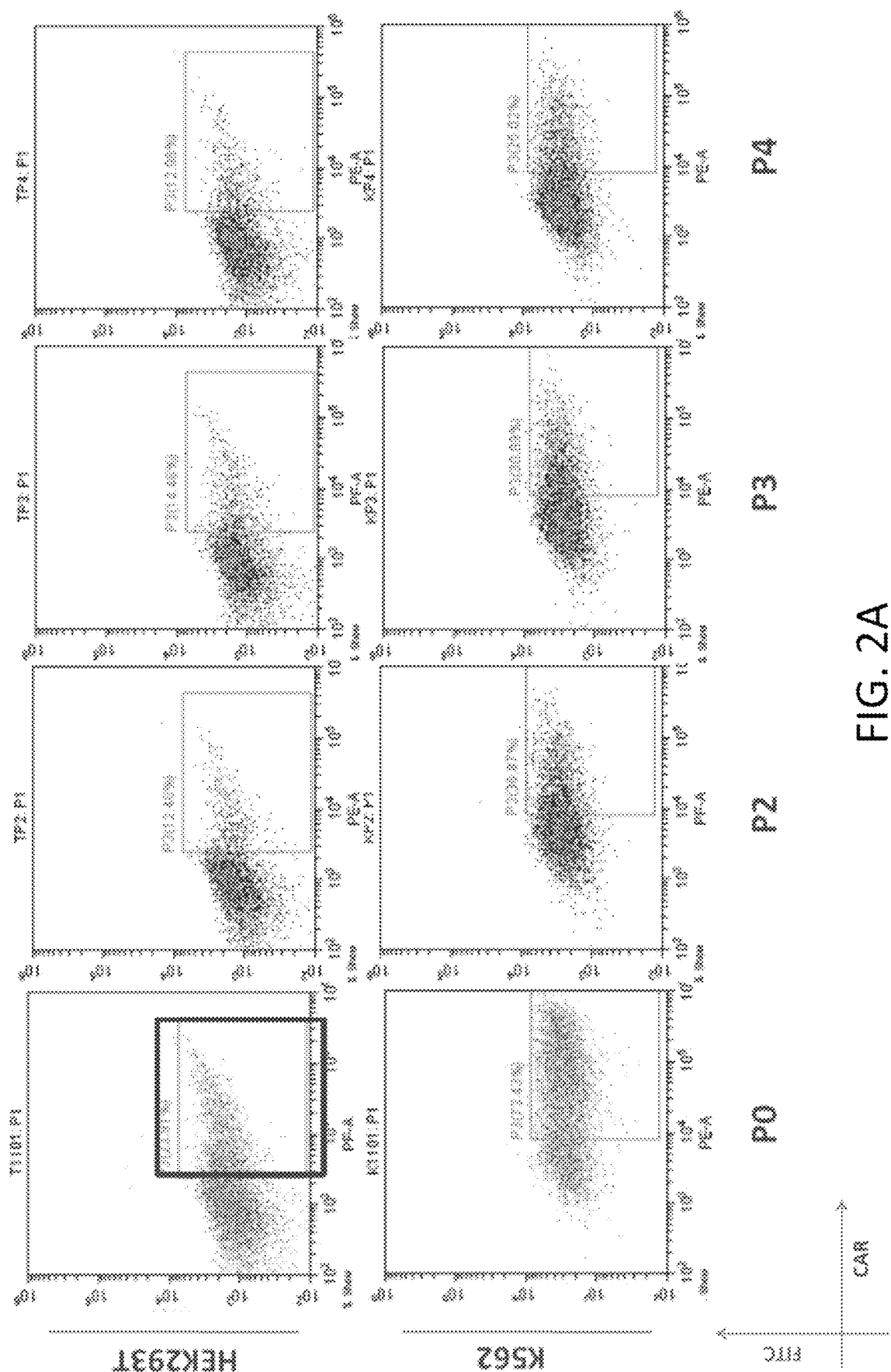
FIGS. 2A and 2B, is a series images showing expression of CAR and modified PD-1 on transduced 293T and K562 cells.

The present disclosure relates to the discovery that immune tolerance induced by PD-L1 on CAR T cells based therapy can be reduced by expression of genetically modified PD-1 on these T cells. In some embodiments, these T cells include a nucleic acid sequence that encodes CAR and genetically modified PD-1 such that the modified PD-1 and the CAR are expressed as gene products that are separate polypeptides on these T cells. An example of the genetic modification includes substitution or deletion of one or more nucleotides associated with expression or a function of an intracellular part of PD-1.

In some embodiments, the present disclosure provides a T cell engineered to express CAR against CD19 and modified PD-1 such that an inhibitory effect of PD-L1 on cytokine production of the T cell is significantly less than an inhibitory effect of PD-L1 on cytokine production of a T cell that does not include at least a part of the nucleic acid sequence that encodes the modified PD-1. In some instances, the CAR is specific for a tumor antigen that is present on a tumor cell, and the tumor cell expresses PD-L1. Therefore, the engineered T cell of the present disclosure when infused into a patient can reduce immune tolerance induced by PD-L1 of tumor cells and further eliminate these tumor cells in vivo in the patient.

Definitions

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e. to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody" is used in the broadest sense and specifically covers monoclonal antibodies (including full-length monoclonal antibodies), multispecific antibodies (e.g., bispecific antibodies), and antibody fragments so long as they exhibit the desired biological activity or function. The antibodies in the present disclosure may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

"Antibody fragments" comprise a portion of a full-length antibody, generally the antigen-binding or variable region of the antibody. Examples of antibody fragments include Fab, Fab', F(ab')2, and Fv fragments; diabodies; linear antibodies; single-chain antibody molecules; and multispecific antibodies formed from antibody fragments.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of a Fv including only three complementarity determining regions (CDRs) specific for an antigen) has the ability to recognize and bind antigen, although at a lower affinity than the entire binding site. An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response, which may involve either antibody production, or the activation of specific immunologically competent cells, or both. Antigens may include any macromolecule, including virtually all proteins or peptides, or molecules derived from recombinant or genomic DNA. For example, DNA including a nucleotide sequence or a partial nucleotide sequence encoding a protein that elicits an immune response, therefore, encodes an "antigen" as that term is used herein. Furthermore, an antigen need not be encoded solely by a full-length nucleotide sequence of a gene. Further, an antigen can be generated, synthesized or derived from a biological sample including a tissue sample, a tumor sample, a cell or a biological fluid.

The term "anti-tumor effect" as used herein, refers to a biological effect associated with a decrease in tumor volume, a decrease in the number of tumor cells, a decrease in the number of metastases, an increase in life expectancy of a subject having tumor cells, or amelioration of various physiological symptoms associated with the cancerous condition. An "anti-tumor effect" can also be manifested by the ability of the peptides, polynucleotides, cells and antibodies of the disclosure in the prevention of the occurrence of tumor in the first place.

The term "auto-antigen" refers to an antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from the same individual to which it is later to be re-introduced into the individual.

"Allogeneic" is used to describe a graft derived from a different animal of the same species.

"Xenogeneic" is used to describe a graft derived from an animal of a different species.

The term "cancer" as used herein is defined as a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer et al.

Throughout this specification, unless the context requires otherwise, the words "comprise," "includes" and "including" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but those other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands.

By "corresponds to" or "corresponding to" is meant (a) a polynucleotide having a nucleotide sequence that is substantially identical or complementary to all or a portion of a reference polynucleotide sequence or encoding an amino acid sequence identical to an amino acid sequence of a peptide or protein; or (b) a peptide or polypeptide having an amino acid sequence that is substantially identical to a sequence of amino acids in a reference peptide or protein.

"Co-stimulatory ligand," includes a molecule on an antigen presenting cell (e.g., an APC, dendritic cell, B cell, et al.) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including proliferation, activation, differentiation, et al. A co-stimulatory ligand can include CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as CD27, CD28, 4-1BB, OX40, CD30, CD40, PD-1, ICOS, lymphocyte function associated antigen-1 (LFA-1), CD2, CD7, LIGHT, NKG2C, B7-H3, and a ligand that specifically binds to CD83.

A "co-stimulatory molecule" refers to the cognate binding partner on a T cell that specifically binds to a costimulatory ligand, thereby mediating a co-stimulatory response by the T cell, such as proliferation. Co-stimulatory molecules include an MHC class I molecule, BTLA and a Toll-like receptor.

A "co-stimulatory signal" refers to a signal, which in combination with a primary signal, such as TCR/CD3 ligation, leads to T cell proliferation and/or upregulation or down regulation of key molecules.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians. As used herein, a "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "effective" means adequate to accomplish a desired, expected, or intended result. For example, an "effective amount" may be an amount of a compound sufficient to produce a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

With regard to polynucleotides, the term "exogenous" refers to a polynucleotide sequence that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides, the term "endogenous" or "native" refers to naturally-occurring polynucleotide sequences that may be found in a given wild-type cell or organism. Also, a particular polynucleotide sequence that is isolated from a first organism and transferred to the second organism by molecular biological techniques is typically considered an "exogenous" polynucleotide with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" as used herein is defined as the transcription and/or translation of a particular nucleotide sequence driven by its promoter.

"Expression vector" refers to a vector including a recombinant polynucleotide including expression control sequences operatively linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

By "isolated" is meant a material that is substantially or essentially free from components that normally accompany it in its native state. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

The nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," et al. are used interchangeably herein, and refer to any animal, or cells thereof whether in vitro or in situ, amenable to the methods described herein. In certain non-limiting embodiments, the patient, subject or individual is a human. In some embodiments, the term "subject" is intended to include living organisms in which an immune response can be elicited (e.g., mammals). Examples of subjects include humans, dogs, cats, mice, rats, and transgenic species thereof.

The recitation "polynucleotide" or "nucleic acid" as used herein designates mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes single and double stranded forms of DNA and RNA.

The terms "polynucleotide variant" and "variant" and the like refer to polynucleotides displaying substantial sequence identity with a reference polynucleotide sequence or polynucleotides that hybridize to a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide, or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs that encode these enzymes.

"Polypeptide," "polypeptide fragment," "peptide" and "protein" are used interchangeably herein to refer to a polymer of amino acid residues and to variants and synthetic analogs of the same. Thus, these terms apply to amino acid polymers in which one or more amino acid residues are synthetic non-naturally occurring amino acids, such as a chemical analog of a corresponding naturally occurring amino acid, as well as to naturally occurring amino acid polymers. In certain aspects, polypeptides may include enzymatic polypeptides, or "enzymes," which typically catalyze (i.e., increase the rate of) various chemical reactions.

The recitation polypeptide "variant" refers to polypeptides that are distinguished from a reference polypeptide sequence by the addition, deletion or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard; it is well understood in the art that some amino acids may be changed to others with broadly similar properties without changing the nature of the activity of the polypeptide. Polypeptide variants also encompass polypeptides in which one or more amino acids have been added or deleted, or replaced with different amino acid residues.

The term "promoter" as used herein is defined as a DNA sequence recognized by the synthetic machinery of the cell or introduced synthetic machinery, required to initiate the specific transcription of a polynucleotide sequence. The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" means that one molecule recognizes and adheres to a particular second molecule in a sample or organism, but does not substantially recognize or adhere to other structurally unrelated molecules in the sample. By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross-reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

A "soluble receptor" is a receptor polypeptide that is not bound to a cell membrane. Soluble receptors are most commonly ligand-binding receptor polypeptides that lack transmembrane and cytoplasmic domains. Soluble receptors may include additional amino acid residues, such as affinity tags that provide for purification of the polypeptide or provide sites for attachment of the polypeptide to a substrate, or immunoglobulin constant region sequences. Many cell-surface receptors have naturally occurred, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

By the term "stimulation," is meant a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures et al.

A "stimulatory molecule" refers to a molecule on a T cell that specifically binds to a cognate stimulatory ligand present on an antigen presenting cell.

A "stimulatory ligand" refers to a ligand that when present on an antigen presenting cell (e.g., an APC, a dendritic cell, a B-cell, et al.) can specifically bind with a cognate binding partner (referred to herein as a "stimulatory molecule") on a T cell, thereby mediating a primary response by the T cell, including activation, initiation of an immune response, proliferation, et al. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to a cell that has been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease, and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which includes an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes et al. Examples of viral vectors include, but are not limited to, adenoviral vectors, adeno-associated virus vectors, retroviral vectors, et al. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiple attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The present disclosure relates to isolated nucleic acid sequences, vectors including the isolated nucleic acid sequences, cells including the isolated nucleic acid sequences and methods of treating cancer using these cells.

Compositions and Therapeutic Application

Embodiments herein relate to an isolated nucleic acid sequence including a nucleic acid sequence that encodes modified programmed cell death protein 1 (PD-1) and a nucleic acid sequence that encodes chimeric antigen receptor (CAR). In some embodiments, the modified PD-1 and the CAR are expressed as gene products that are separate polypeptides. In these instances, the CAR is specific for a tumor antigen that is present on a cancer cell, and the cancer cell expresses PD-L1.

CARs are molecules generally including an extracellular and intracellular domain. The extracellular domain includes a target-specific binding element. The intracellular domain (e.g., cytoplasmic domain) includes a costimulatory signaling region and a zeta chain portion. The costimulatory signaling region refers to a portion of the CAR including the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain of the polypeptide chain. A spacer domain may include up to 300 amino acids, preferably 10 to 100 amino acids and most preferably 25 to 50 amino acids.

In some embodiments, the target-specific binding element of the CAR in the present disclosure may recognize a tumor antigen. Tumor antigens are proteins that are produced by tumor cells that elicit an immune response, particularly T-cell mediated immune responses. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxylesterase, mut hsp70-2, M-CSF, prostase, prostate-specific antigen (PSA), PAP, NY-ESO-1, LAGE-1a, p53, prostein, PSMA, Her2/neu, survivin and telomerase, prostate carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen includes HER2, CD19, CD20, CD22, Kappa or light chain, CD30, CD33, CD123, CD38, ROR1, ErbB3/4, EGFR, EGFRvIII, EphA2, FAP, carcinoembryonic antigen, EGP2, EGP40, mesothelin, TAG72, PSMA, NKG2D ligands, B7-H6, IL-13 receptor α 2, IL-11 receptor α, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, CD44v6, TEM1, TEM8, or viral-associated antigens expressed by the tumor.

In some embodiments, the antigen binding element of the CAR of the disclosure targets CD19. In some instances, the antigen binding element of the CAR of the disclosure includes anti-CD19 scFV including the nucleic acid sequence set forth in SEQ ID NO: 1.

In some embodiments, the transmembrane domain of the CAR of the disclosure includes the CD8 or CD9 transmembrane domain. In some embodiments, the intracellular domain of the CAR of the disclosure includes the intracellular domain of 4-1BB (CD137) or CD 28. PD-1, a member of the CD28 family, is a type 1 transmembrane protein with the extracellular domain containing a single immunoglobulin (Ig)-like variable domain and the intracellular domain containing an immunoreceptor tyrosine-based inhibitory motif. PD-1 is expressed on activated T-cells, B-lymphocytes, natural killer cells, dendritic cells, and activated monocytes. The interaction between PD-1 and its ligands PD-L1 and PD-L2 leads to T-cell exhaustion, inactivation, and apoptosis.

Exhausted T lymphocytes lose the ability to produce proinflammatory cytokines including IL-2, tumor necrosis factor-α, and interferon-γ. Expression of PD-L1 by diverse tissues mediates peripheral immune tolerance, and activation of the PD-1/PD-L1 axis limits the tissue damage after a sustained immune/inflammatory response. PD-1-expressing tumor-infiltrating lymphocytes are associated with an impaired antitumor effect and upregulation of PD-1, and PD-L1 is associated with outcome in several tumor types.

The embodiments relate to an isolated nucleic acid sequence including a nucleic acid sequence that encodes modified PD-1 and a nucleic acid sequence that encodes chimeric antigen receptor (CAR). In some embodiments, the nucleic acid sequence encoding modified PD-1 may include substitution or deletion of one or more nucleotides as compared to a nucleic acid sequence encoding an intracellular part of wild-type PD-1. In certain embodiments, the nucleic acid sequence that encodes the modified PD-1 includes deletion of one or more nucleotides as compared to a nucleic acid sequence encoding an intracellular part of wild-type PD-1. For example, the modified PD-1 is human PD-1 that includes the amino acid sequence of SEQ ID NO: 14.

In some embodiments, the nucleic acid sequence that encodes the modified PD-1 includes a nucleic acid encoding a truncated PD-1 that does not include an intracellular domain. For example, the nucleic acid sequence that encodes the modified PD-1 includes the amino acid sequence of SEQ ID NO: 12.

In some embodiments, the modified PD-1 includes one or more point mutations as compared to wild-type PD-1. In certain embodiments, point mutations may include one or two amino acid point mutations of phosphorylation sites of wild-type PD-1. For example, the amino acid point mutations include a point mutation of Tyrosine residue 223, and/or Tyrosine residue 248.

The embodiments of the present disclosure further relate to a DNA construct including sequences encoding a CAR and a modified PD-1. In some embodiments, the CAR can include any combination of CD3-zeta, CD28, 4-1BB et al. For example, the CAR of the disclosure includes anti-CD19 scFv, human CD8 hinge and transmembrane domain, and human 4-1BB and CD3zeta signaling domains. In one embodiment, the CAR of the disclosure includes the nucleic acid sequence set forth in SEQ ID NO: 1.

In some embodiments, internal ribosome entry sites (IRES) elements are used to create multigene, or polycistronic, or messages. For example, an IRES element may link a nucleic acid sequence encoding CAR and a nucleic acid sequence encoding one of the various modified PD-1 (See Table 1).

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

The embodiments of the present disclosure further relate to vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

The expression of natural or synthetic nucleic acids encoding CARs and modified PD-1 is typically achieved by operably linking a nucleic acid encoding the CAR polypeptide or portions thereof to one or more promoters, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

Additional information related to expression synthetic nucleic acids encoding CARs and modified PD-1s and gene transfer into mammalian cells is provided in U.S. Pat. No. 8,906,682, incorporated by reference in its entirety.

The embodiments further relate to genetically modified cells (e.g., T cells) expressing a CAR and a modified PD-1. In some embodiments, a dominant negative PD-1 is introduced into the T cells such that the dominant negative PD-1 inhibits wild-type PD-1 activity induced by PD-L1 of a tumor cell. In certain embodiments, the genetically modified T cells express non-functional PD-1. For example, the genetically modified T cells express PD-1 molecules, not including intracellular domain, not including both intracellular and transmembrane domains, or including a point mutation as described in the present disclosure.

In some embodiments, an inhibitory effect of PD-L1 of a tumor cell on cytokine production of the genetically modified T cells of the present disclosure is less than an inhibitory effect of PD-L1 on cytokine production of T cells that do not include at least a part of the nucleic acid sequence that encodes the modified PD-1. For example, an inhibitory effect of PD-L1 on cytokine production of the genetically modified T cells of the present disclosure is sufficient to reduce at least 5%, at least 10%, at least 15%, at least 20%, at least 30%, at least 40%, at least 50%, at least 60%, at least 70%, at least 80%, at least 90% of an inhibitory effect of PD-L1 on cytokine production of T cells that do not include at least a part of the nucleic acid sequence that encodes the modified PD-1.

In some embodiment, the genetically modified T cells include a nucleic acid sequence that encodes the modified PD-1 having one or more point mutations as compared to wild-type PD-1. For example, the point mutation comprises one or two amino acid point mutations of phosphorylation sites of wild-type PD-1. In certain embodiments, the genetically modified T cells include the nucleic acid sequence that encodes the modified PD-1 and includes deletion of one or more nucleotides as compared to a nucleic acid sequence encoding an intracellular part of wild-type PD-1. For example, the nucleic acid sequence that encodes the modified PD-1 comprises the amino acid sequence of SEQ ID NO: 12 or SEQ ID NO: 14.

The embodiments further relate to methods for treating a patient for an illness including administering to the patient an effective amount of the engineered cells of the present disclosure. Various illnesses can be treated according to the present methods including cancer, such as ovarian carcinoma, breast carcinoma, colon carcinoma, glioblastoma multiforme, prostate carcinoma and leukemia. In some embodiments, the method includes administering to a human patient a pharmaceutical composition including an antitumor effective amount of a population of human T cells, wherein the human T cells of the population include human T cells that comprises the nucleic acid sequence as described in the present disclosure.

Cancers that may be treated include tumors that are not vascularized, or not yet substantially vascularized, as well as vascularized tumors. The cancers may include non-solid tumors (such as hematological tumors, for example, leukemias and lymphomas) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Generally, the cells activated and expanded as described herein may be utilized in the treatment and prevention of diseases that arise in individuals who are immunocompromised. In particular, the engineered cells of the present disclosure are used in the treatment of cancer. In certain embodiments, the cells of the present disclosure are used in the treatment of patients at risk of developing cancer. Thus, the present disclosure provides methods for the treatment or prevention of cancer comprising administering to a subject in need thereof, a therapeutically effective amount of the engineered T cells of the present disclosure.

The engineered T cells of the present disclosure may be administered either alone or as a pharmaceutical composition in combination with diluents and/or with other components such as IL-2 or other cytokines or cell populations. Briefly, pharmaceutical compositions of the present disclosure may include a target cell population as described herein, in combination with one or more pharmaceutically or physiologically acceptable carriers, diluents or excipients. Such compositions may include buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present disclosure, and reinfuse the patient with these activated and expanded T cells. This process can be carried out multiple times every few weeks. In certain embodiments, T cells can be activated from blood draws off from 10 ccs to 400 ccs. In certain embodiments, T cells are activated from blood draws of 20 cc, 30 ccs, 40 ccs, 50 ccs, 60 ccs, 70 ccs, 80 ccs, 90 ccs, or 100 ccs. Not to be bound by theory, using this multiple blood draw/multiple reinfusion protocols, may select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present disclosure are administered to a patient by intradermal or subcutaneous injection. In another embodiment, the T cell compositions of the present disclosure are preferably administered by i.v. injection. The compositions of T cells may be injected directly into a tumor, lymph node, or site of infection.

In certain embodiments of the present disclosure, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the present disclosure may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium-dependent phosphatase calcineurin (cyclosporine and FK506) or inhibit the p7056 kinase that is important for growth factor-induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In a further embodiment, the cell compositions of the present disclosure are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present disclosure are administered following B-cell ablative therapy such as agents that react with CD20, e.g., Rituxan. For example, in one embodiment, subjects may undergo standard treatment with high-dose chemotherapy followed by peripheral blood stem cell transplantation. In certain embodiments, following the transplant, subjects receive an infusion of the expanded immune cells of the present disclosure. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period of 1 and 30 days. The preferred daily dose is 1 to 10 mg per day although, in some instances, larger doses of up to 40 mg per day may be used (described in U.S. Pat. No. 6,120,766, incorporated by reference in its entirety).

Additional information on the methods of cancer treatment using engineer T cells is provided in U.S. Pat. No. 8,906,682, incorporated by reference in its entirety.

The embodiments further relate to a method of treating and/or inhibiting cancer of a subject. The method includes administering to the subject a therapeutically effective amount of a soluble receptor including an extracellular domain of PD-1. In some embodiments, the soluble receptor binds a PD-L1 protein, and the soluble receptor disrupts PD-1 signaling of cancer cells and/or disrupts PD-1 binding to PD-L1. In certain embodiments, the isolated soluble receptor polypeptide includes the amino acid residues of SEQ ID NO:9.

A "soluble receptor" is a receptor polypeptide that is not bound to a cell membrane. Soluble receptors are most commonly ligand-binding receptor polypeptides that lack transmembrane and cytoplasmic domains. Soluble receptors may include additional amino acid residues, such as affinity tags that provide for purification of the polypeptide or provide sites for attachment of the polypeptide to a substrate, or immunoglobulin constant region sequences. Many cell-surface receptors have naturally occurred, soluble counterparts that are produced by proteolysis. Soluble receptor polypeptides are said to be substantially free of transmembrane and intracellular polypeptide segments when they lack sufficient portions of these segments to provide membrane anchoring or signal transduction, respectively.

The embodiments further related to modified cell including a receptor polypeptide, a cytoplasmic domain of the receptor polypeptide being truncated, the receptor polypeptide being at least one of a Programmed cell death protein 1 (PD-1) receptor polypeptide, cytotoxic T-lymphocyte-associated protein 4 (CTLA-4) receptor polypeptide, or B- and T-lymphocyte attenuator (BTLA) receptor.

The embodiments further relate to a method for treating a subject having a disease. The method includes administering a cell to the subject having the disease, wherein the cell is genetically modified to express a receptor polypeptide, a cytoplasmic domain of the receptor polypeptide being truncated, the receptor polypeptide being at least one of a Programmed cell death protein 1 (PD-1) receptor polypeptide, cytotoxic T-lymphocyte-associated protein 4 (CTLA-4) receptor polypeptide, or B- and T-lymphocyte attenuator (BTLA) receptor; and a chimeric antigen receptor (CAR) including an antigen recognition domain of a specific antibody and an intracellular domain or a modified or wild-type T cell receptor, the specific antibody binding to an antigen.

In some embodiments, the receptor polypeptide is the PD-1 receptor polypeptide, and wherein the cytoplasmic domain of the PD-1 receptor polypeptide contains an immunoreceptor tyrosine-based motif.

The embodiments further relate to modified cell including a reduced amount of one or more receptors as compared to a corresponding wild-type cell, the one or more receptors including at least one of a Programmed cell death protein 1 (PD-1), cytotoxic T-lymphocyte-associated protein 4 (CTLA-4), or B- and T-lymphocyte attenuator (BTLA).

The embodiments further relate to a method for treating a subject having a disease. The method includes administering a cell to the subject having the disease, wherein the cell is modified to express a reduced amount of one or more receptors as compared to a corresponding wild-type cell, the one or more receptors including at least one of a Programmed cell death protein 1 (PD-1), cytotoxic T-lymphocyte-associated protein 4 (CTLA-4), or B- and T-lymphocyte attenuator (BTLA).

In some embodiments, modified cell further includes a chimeric antigen receptor (CAR) including an antigen recognition domain of a specific antibody and an intracellular domain, or a modified or wild-type T cell receptor. In certain embodiments, the modified cell further includes a chimeric antigen receptor (CAR) including an antigen recognition domain of a specific antibody and an intracellular domain or a modified or wild-type T cell receptor, the specific antibody binding to an antigen.

In some embodiments, the modified cell has reduced expression of one or more genes associated with a biosynthesis pathway or transportation pathway of the one or more receptors as compared to the corresponding wild-type cell, or a combination thereof. In certain embodiments, the modified cell includes a disruption of the one or more genes. In certain embodiments, the modified cell includes a partial or a complete deletion of the one or more genes. In certain embodiments, the genetically modified cell replicate in vivo in the human patient.

In some embodiments, the modified cell from memory cells in the human patient. In these instances, the modified cells are administered intravenously to the human patient. In certain embodiments, the modified cells persist in the human patient. For example, the modified cell is an autologous T cell. For another example, the cell may include at least one of a B cell, a T cell, an NK cell, an embryonic cell, or a dendritic cell.

In some embodiments, the disease may include at least one of cancer, immune deficiencies, autoimmune disease, or obesity.

EXAMPLES

The present disclosure is further described with reference to the following examples. These examples are provided for purposes of illustration only and are not intended to be limiting unless otherwise specified. Thus, the present disclosure should in no way be construed as being limited to the following examples, but rather, should be construed to encompass any and all variations which become evident as a result of the teaching provided herein.

Example 1

Expression of CAR and PD-1 on HEK293T & K562 Cells

Lentiviral vectors that encodes a CD19 CAR and a modified PD-1 separated by the encephalomyocarditis virus internal ribosomal entry sequence were generated (see Chimeric Receptors Containing CD137 Signal Transduction Domains Mediate Enhanced Survival of T Cells and Increased Antileukemic Efficacy In Vivo Molecular Therapy vol. 17 no. 8, 1453-1464 August 2009 incorporated herein by reference). Information of DNA constructs encoding CAR and the modified PD-1 is provided in FIG. 1 and Table 1. A summary of these constructs and modules are listed in Tables 1-2.

TABLE 1

DNA constructs and encoding modules

| Ref | Constructs Name | PD-1 Signal Peptide | PD-1 Extracellular domain | PD-1 Transmembrane domain | PD-1 Intracellular domain or residues |
|---|---|---|---|---|---|
| P0 | P0:CD19BBZETAT | No | No | No | No |
| P1 | P1:CD19BBZETAT-ires-soluble PD1 | Yes | Yes | NO | No |
| P2 | P2:CD19BBZETAT-ires-Truncated PD1 | Yes | Yes | Yes | Residues |
| P3 | P3:CD19BBZETAT-ires-point mutation PD1 | Yes | Yes | Yes | Yes: aa223, Y to A; aa248, Y to A |
| P4 | P4:CD19BBZETAT-ires-Deletion PD1 | Yes | Yes | Yes | Residues |

Figure 2B:
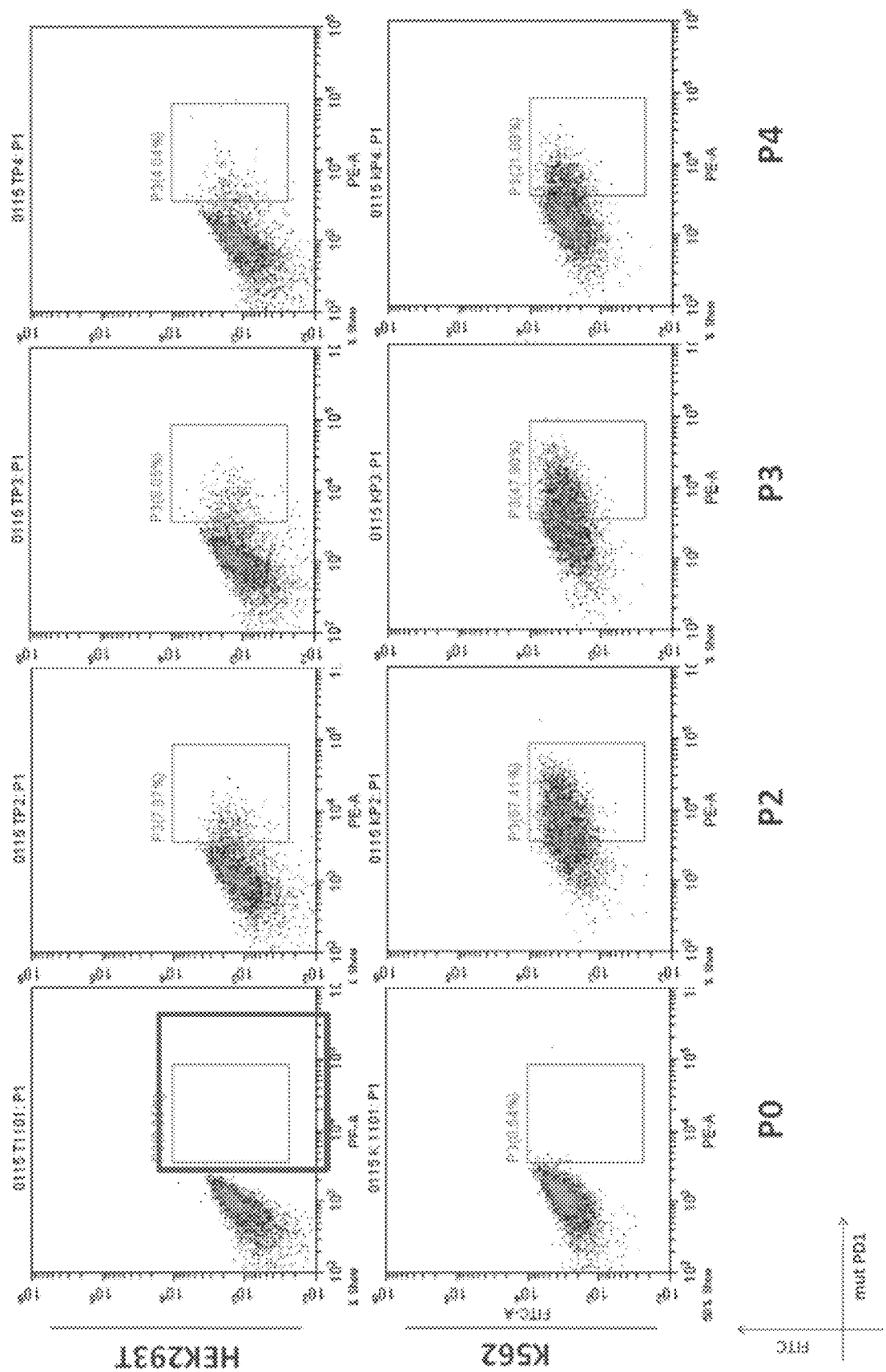

HEK293T & K562 cells were transduced with lentiviral vectors. Flow-cytometry were acquisition performed and analyzed to determine the expression of CAR and PD-1 in these cells. As shown in FIGS. 2A and 2B, both KECK293T and K562 cells expressed CARs (See Box in FIG. 2A) and PD-1s (See Box FIG. 2B).

HEK293T and K562 cells were obtained from American Type Culture Collection (ATCC; Manassas, Va.). Techniques related to cell cultures, construction of lentiviral vectors, and flow cytometry may be found in Chimeric Receptors Containing CD137 Signal Transduction Domains Mediate Enhanced Survival of T Cells and Increased Antileukemic Efficacy In Vivo Molecular Therapy vol. 17 no. 8, 1453-1464 August 2009 incorporated herein by reference, which is incorporated herein by reference.

TABLE 2

Sequence identifiers for various constructs

| SEQ ID NO: # | Identify |
|---|---|
| SEQ ID NO: 1 | P0 (nucleic acid sequence) |
| SEQ ID NO: 2 | P1 (nucleic acid sequence) |
| SEQ ID NO: 3 | P2 (nucleic acid sequence) |
| SEQ ID NO: 4 | P3 (nucleic acid sequence) |
| SEQ ID NO: 5 | P4 (nucleic acid sequence) |
| SEQ ID NO: 6 | IRES element (nucleic acid sequence) |
| SEQ ID NO: 7 | PDL1-IRES-EGFP (nucleic acid sequence) |
| SEQ ID NO: 8 | PD-1 Signal Peptide (amino acid sequence) |
| SEQ ID NO: 9 | PD-1 Extracellular domain (amino acid sequence) |
| SEQ ID NO: 10 | PD-1 Transmembrane domain (amino acid sequence) |
| SEQ ID NO: 11 | P1: added Hydrophilic segment |
| SEQ ID NO: 12 | P2: PD-1 Intracellular domain residues (amino acid sequence) |
| SEQ ID NO: 13 | P3: PD-1 Intracellular domain residues (amino acid sequence) |
| SEQ ID NO: 14 | P4: PD-1 Intracellular domain residues (amino acid sequence) |
| SEQ ID NO: 15 | P2: Removed part of PD-1 Intracellular domain (amino acid sequence) |
| SEQ ID NO: 16 | P4: Removed part of PD-1 Intracellular domain (amino acid sequence) |

Example 2

Expression of CAR and PD-1 on Primary T Cells

Figure 3A:
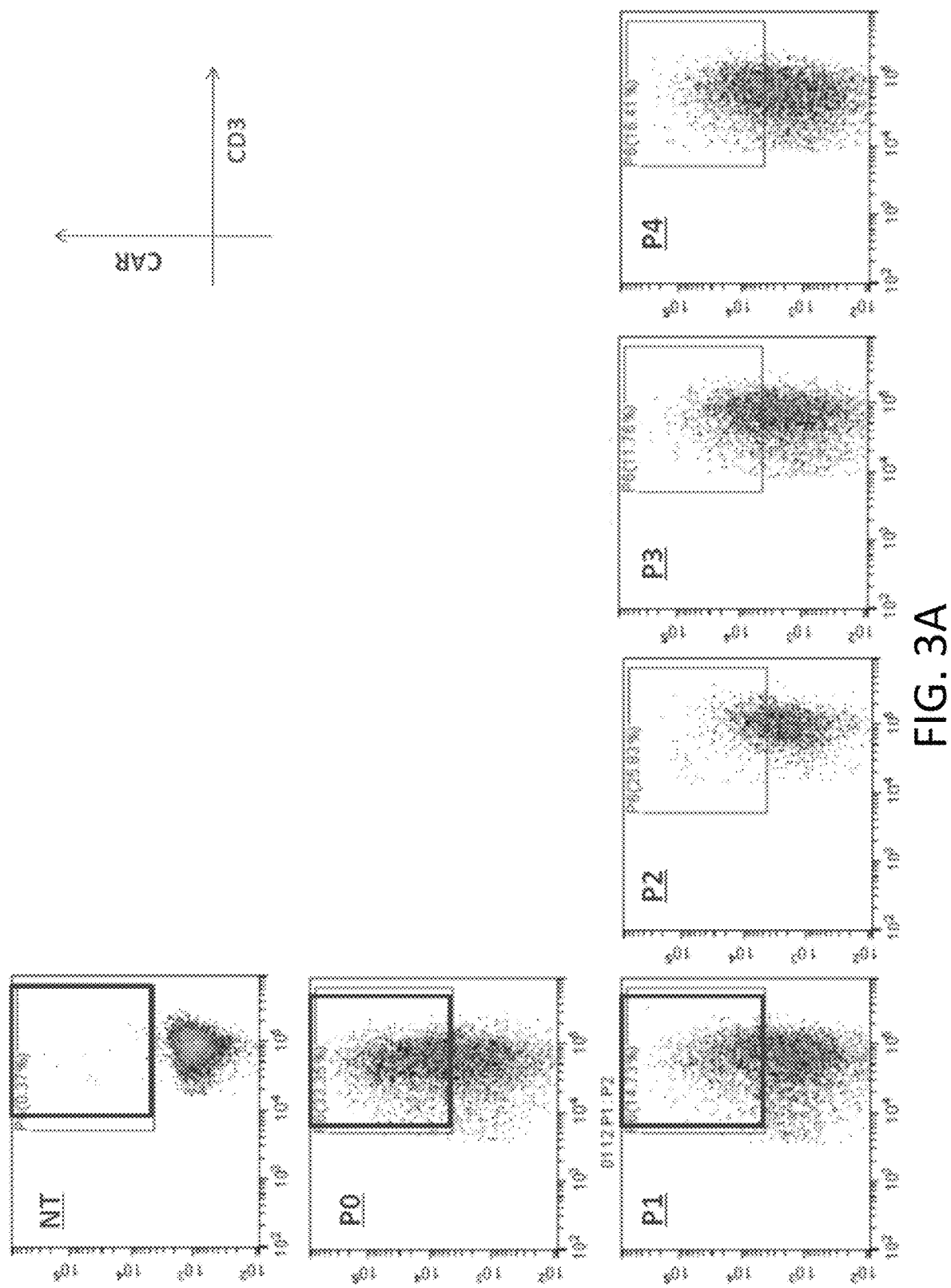
FIGS. 3A through 3C, is a series images showing expression of CAR and modified PD-1 in primary T cells.
Figure 3B:
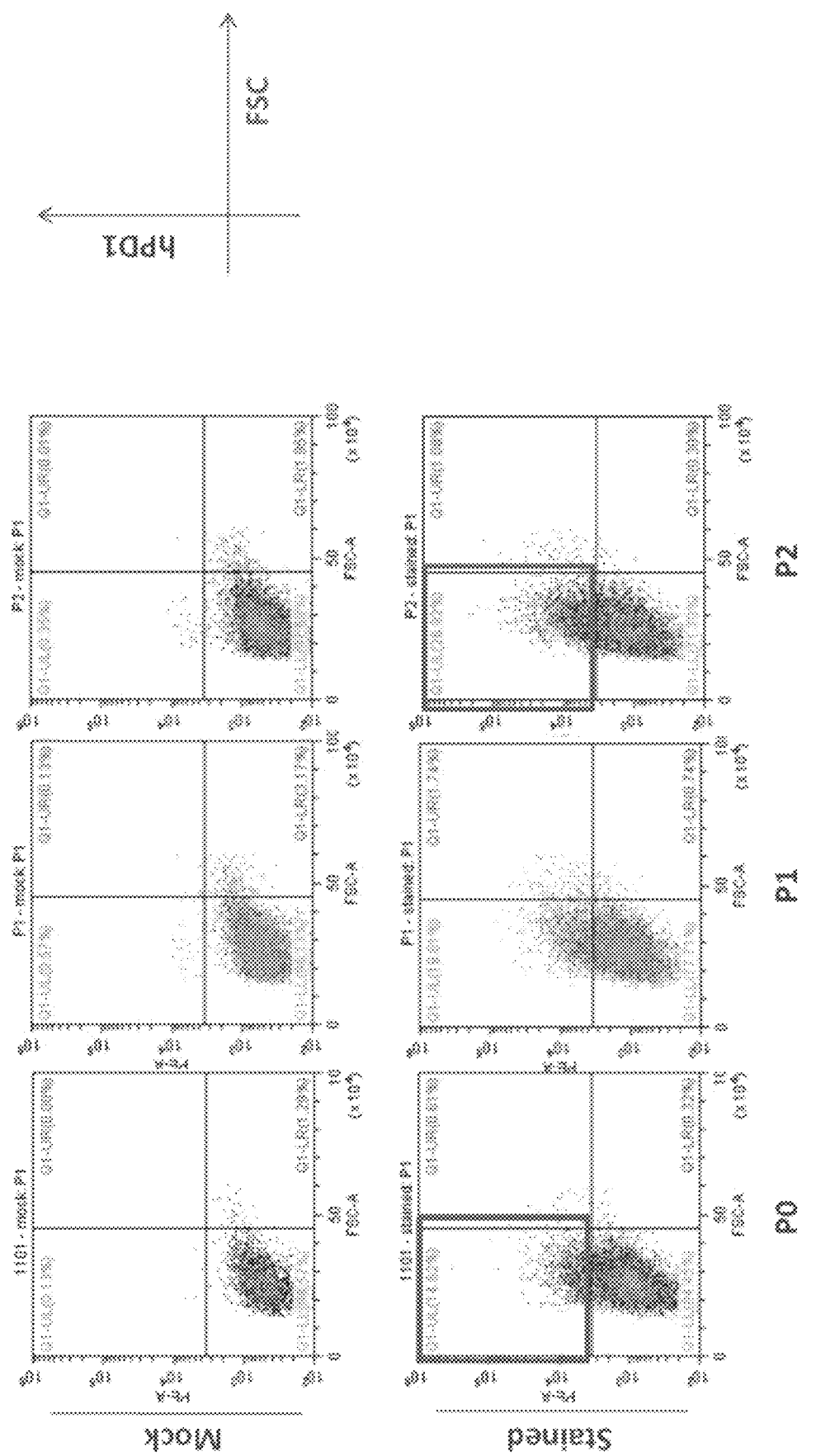
Figure 3C:
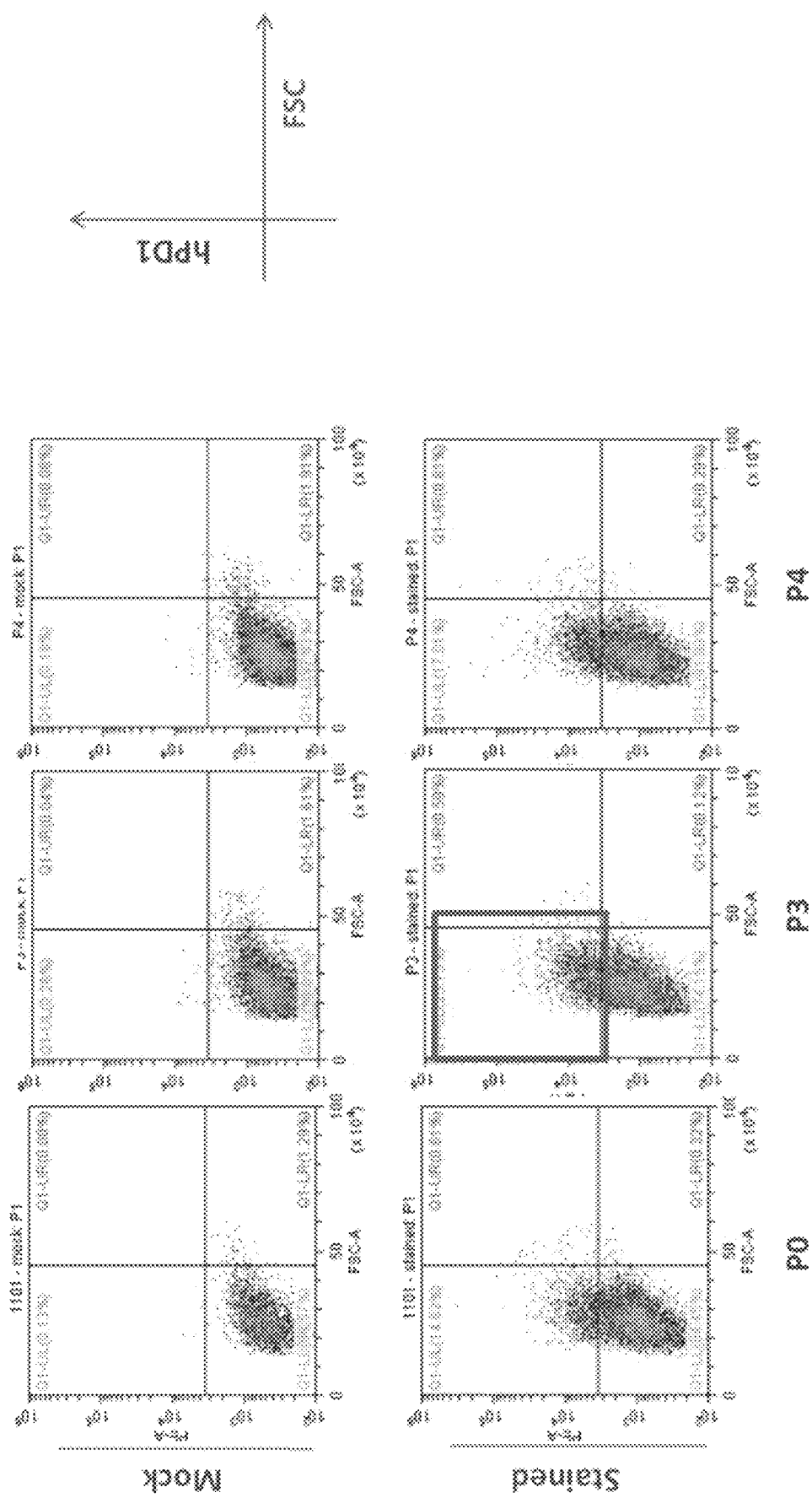

Primary T cells were obtained from patients. The obtained primary T cells were transduced with lentiviral vectors. Flow-cytometry were acquisition was performed and analyzed to determine the expression of CAR and PD-1 in primary T cells. As shown in FIGS. 3A, 3B, and 3C, primary T cells expressed CARs (See Box in FIG. 3A) and PD-1s (See Box FIGS. 3B and 3C).

Techniques related to cell cultures, construction of lentiviral vectors, and flow cytometry may be found in Control of large, established tumor xenografts with genetically retargeted human T cells containing CD28 and CD137 domains. 3360-3365 PNAS Mar. 3, 2009, vol. 106 no. 9, which is incorporated herein by reference.

Example 3

Cytotoxic T-Lymphocyte Assay

Figure 4A:
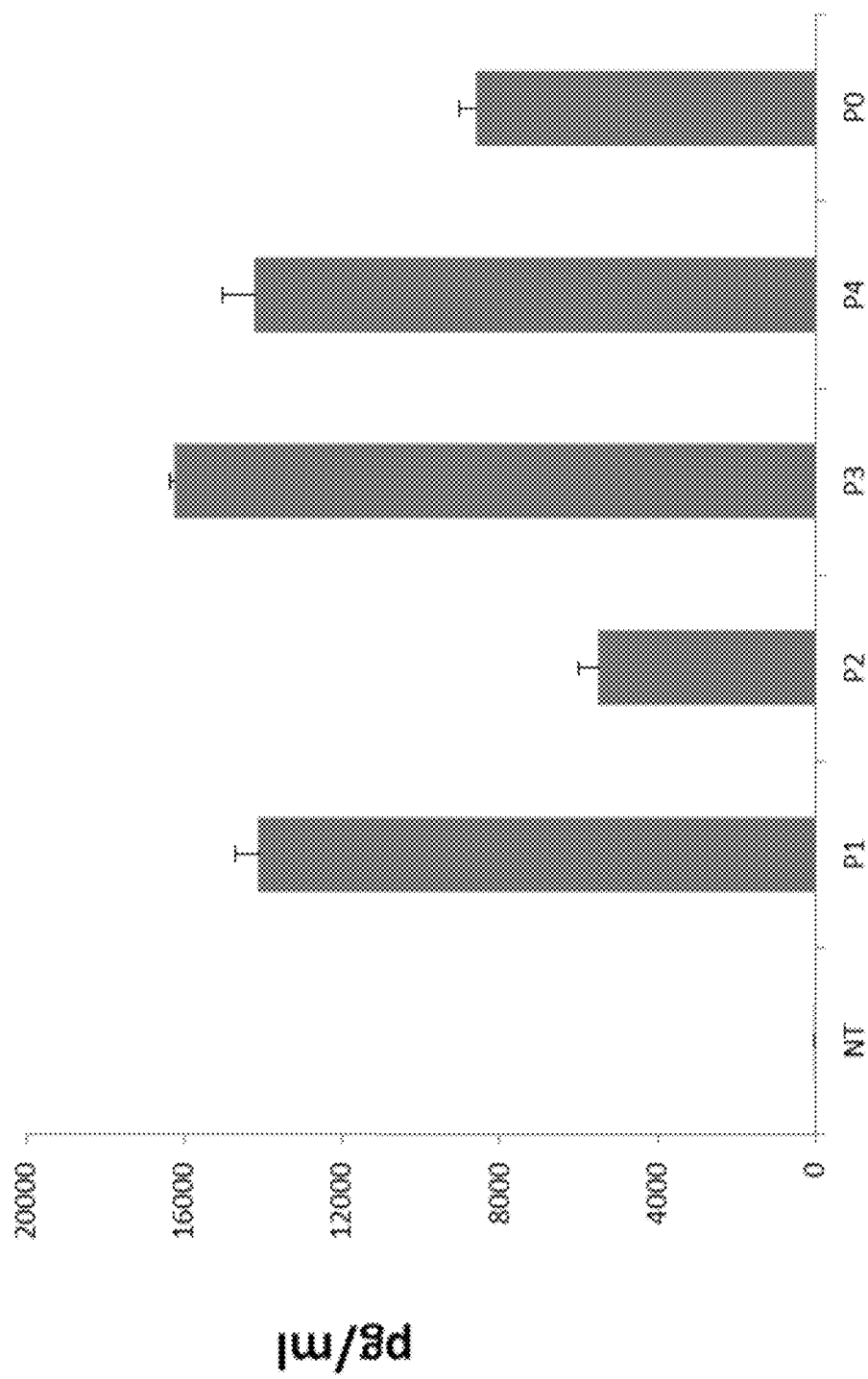
FIG. 4A and FIG. 4B, is a series images showing cytotoxicity of T cells transduced with CAR and modified PF-1.
Figure 4B:
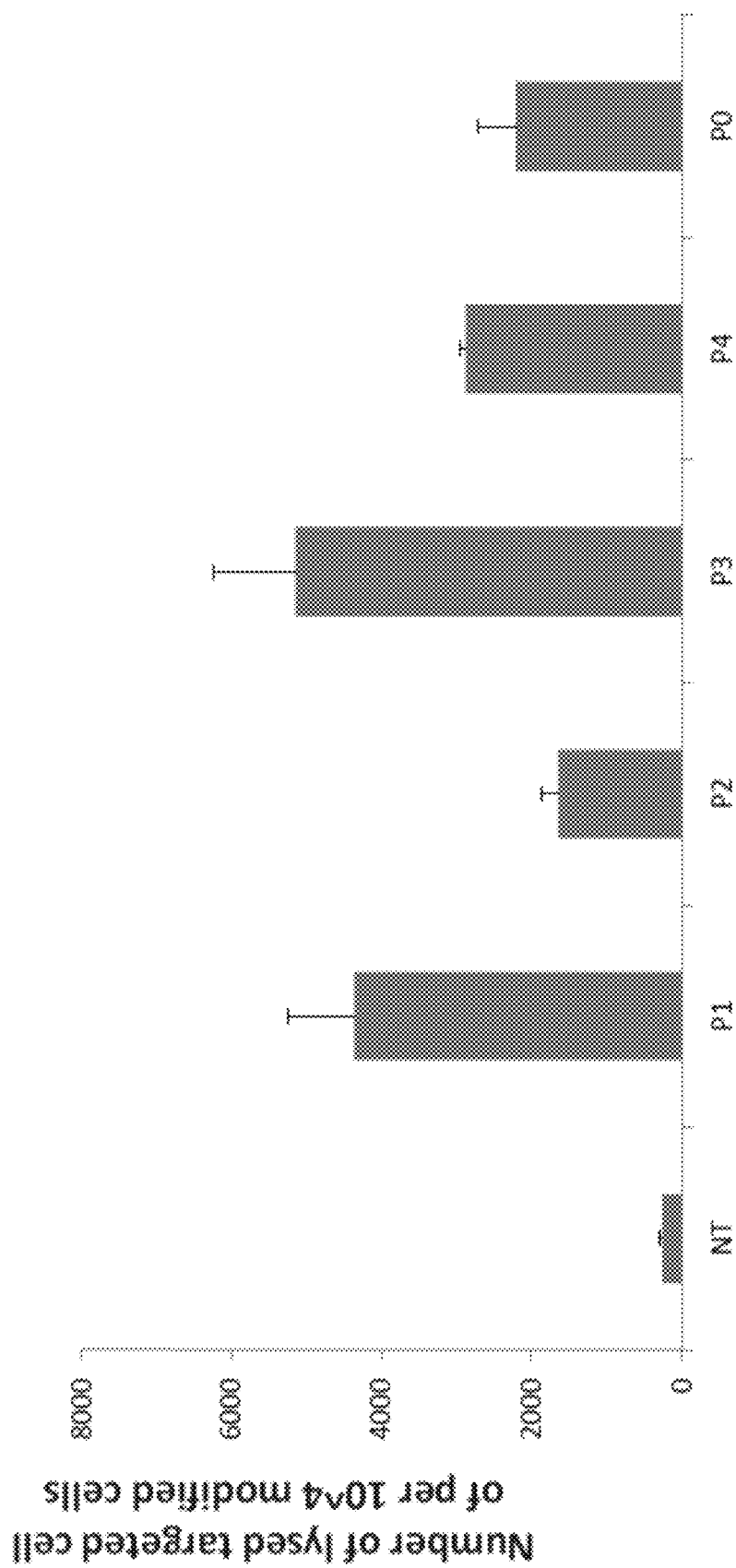

In this assay, the cytotoxicity on target cells (i.e., K562-CD19) is measured by comparing survival of target cells culturing with effector cells (i.e., transduced T cells) relative to the survival of target cells culturing with negative control cells (i.e., non-transduced T cells). Target cells and effector cells or negative control cells were cultured for about 24 hours with a number ratio between the target cells and effector cells or negative control cells being about 10:1. Survival rates of target cells and IFN-gamma production of transduced T cells and non-transduced T cells were measured. As shown in FIGS. 4A and 4B transduced T cells containing nucleic acid sequences encoding CAR, and various PD-1s are capable of releasing IFN-gamma and killing CD19 cells. All error bars are representative of standard deviation.

Techniques related to cell cultures, construction of cytotoxic T-lymphocyte assay may be found in Control of large, established tumor xenografts with genetically retargeted human T cells containing CD28 and CD137 domains. 3360-3365 PNAS Mar. 3, 2009, vol. 106 no. 9, which is incorporated herein by reference.

Example 4

Construction of PD-L1-ires-EGFP Nalm-6 Cell Lines

Figure 5:
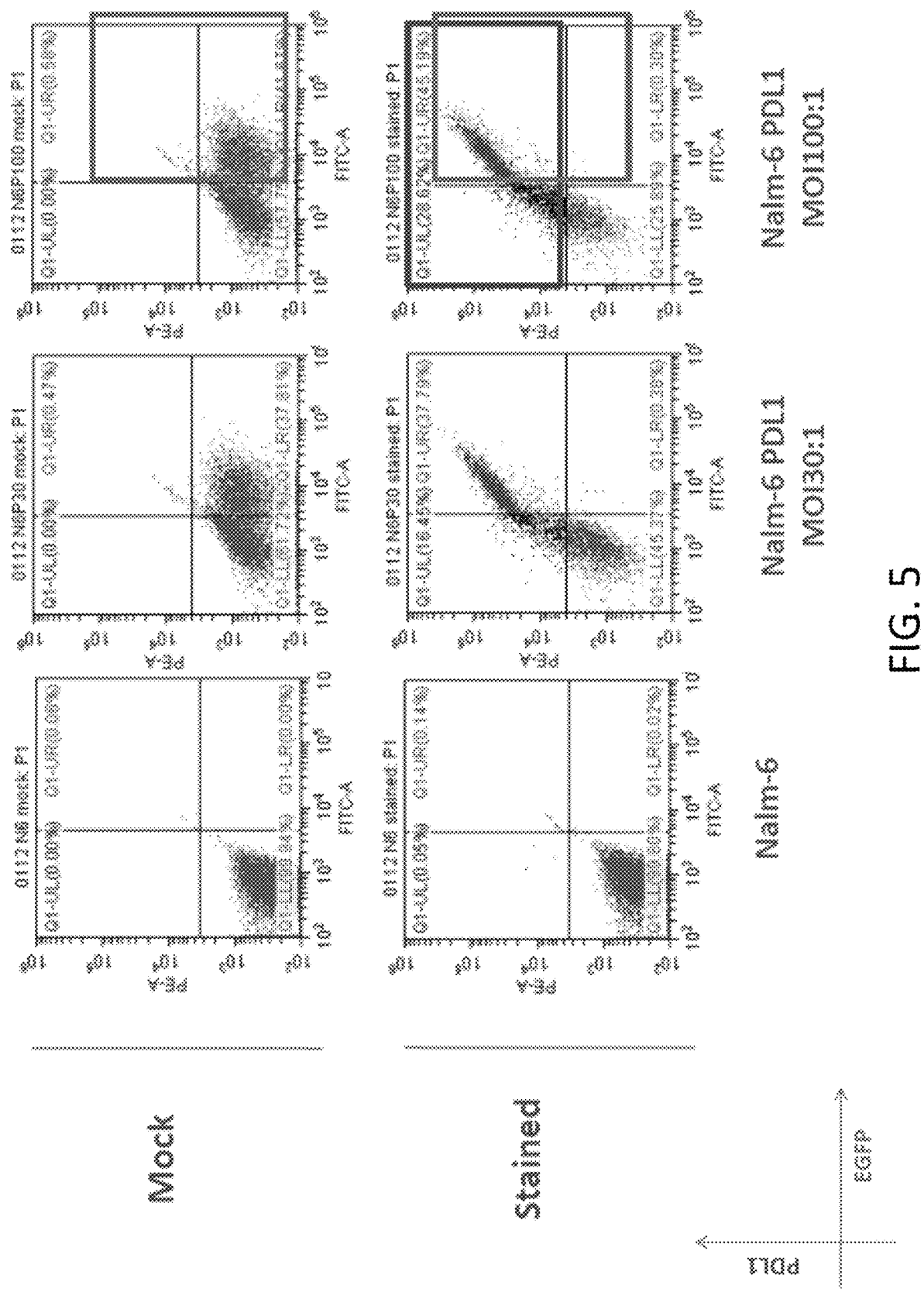
FIG. 5 shows expression of PD-L1 on transduced NalM6 cells.

Lentiviral vectors that encode a PD-L1-ires-EGFP (SEQ ID NO: 7) were generated. Nalm-6 cells were transduced with lentiviral vectors T cells an MOI of 30 or an MOI of 100. Flow-cytometry were acquisition performed and analyzed to determine the expression of CAR and PD-1 in these cells. As shown in FIG. 5, NalM-6 PD-L1 expressed PD-L1.

Nalm-6 cells were obtained from American Type Culture Collection (ATCC; Manassas, Va.). Techniques related to cell cultures, construction of lentiviral vectors, and flow cytometry may be found in Treatment of Advanced Leukemia in Mice with mRNA-Engineered T Cells. HUMAN GENE THERAPY 22:1575-1586 (December 2011), which is incorporated herein by reference.

Example 5

Inhibition of Cytotoxicity Induced by PD-L1 Decreases on T Cells Transduced with CAR and Modified PD-1

Figure 6A:
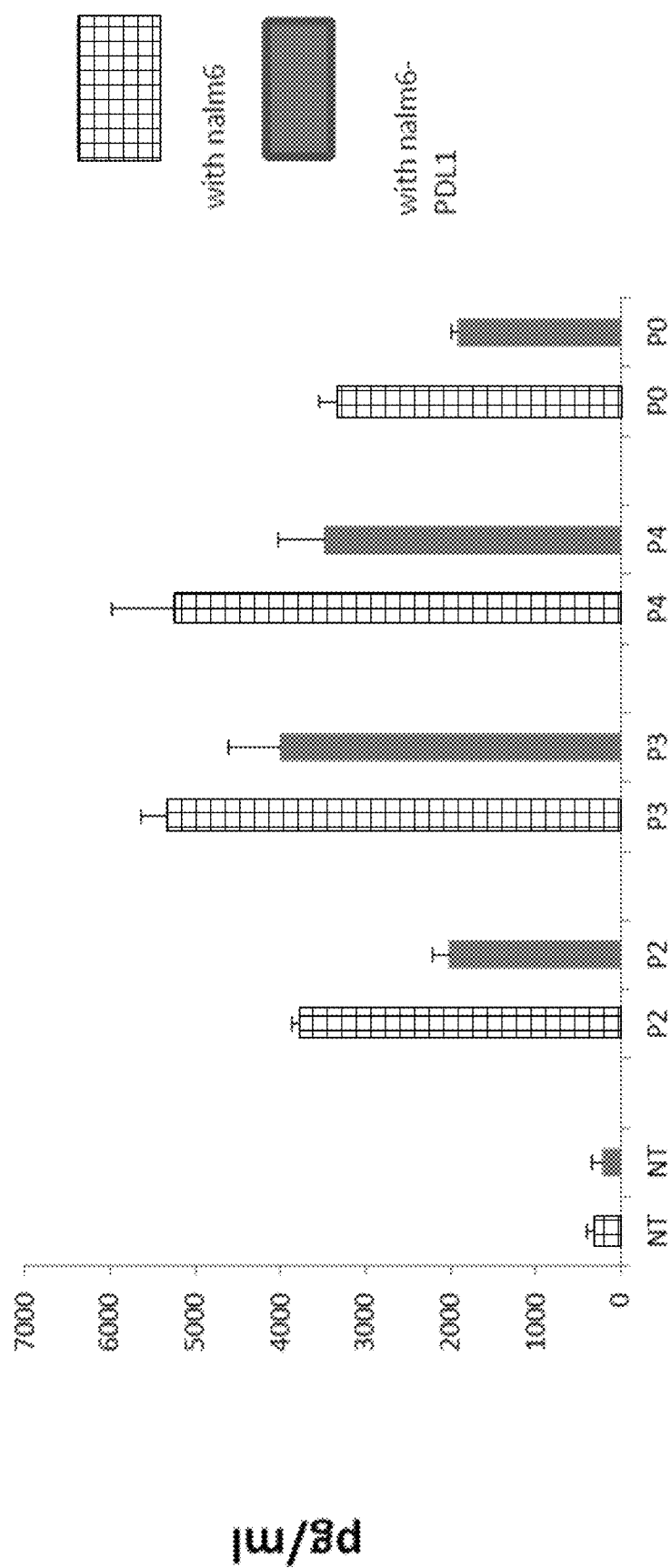
FIGS. 6A and 6B, is series images demonstrating that modified PD-1 reduces immune tolerance induced by PD-L1.
Figure 6B:
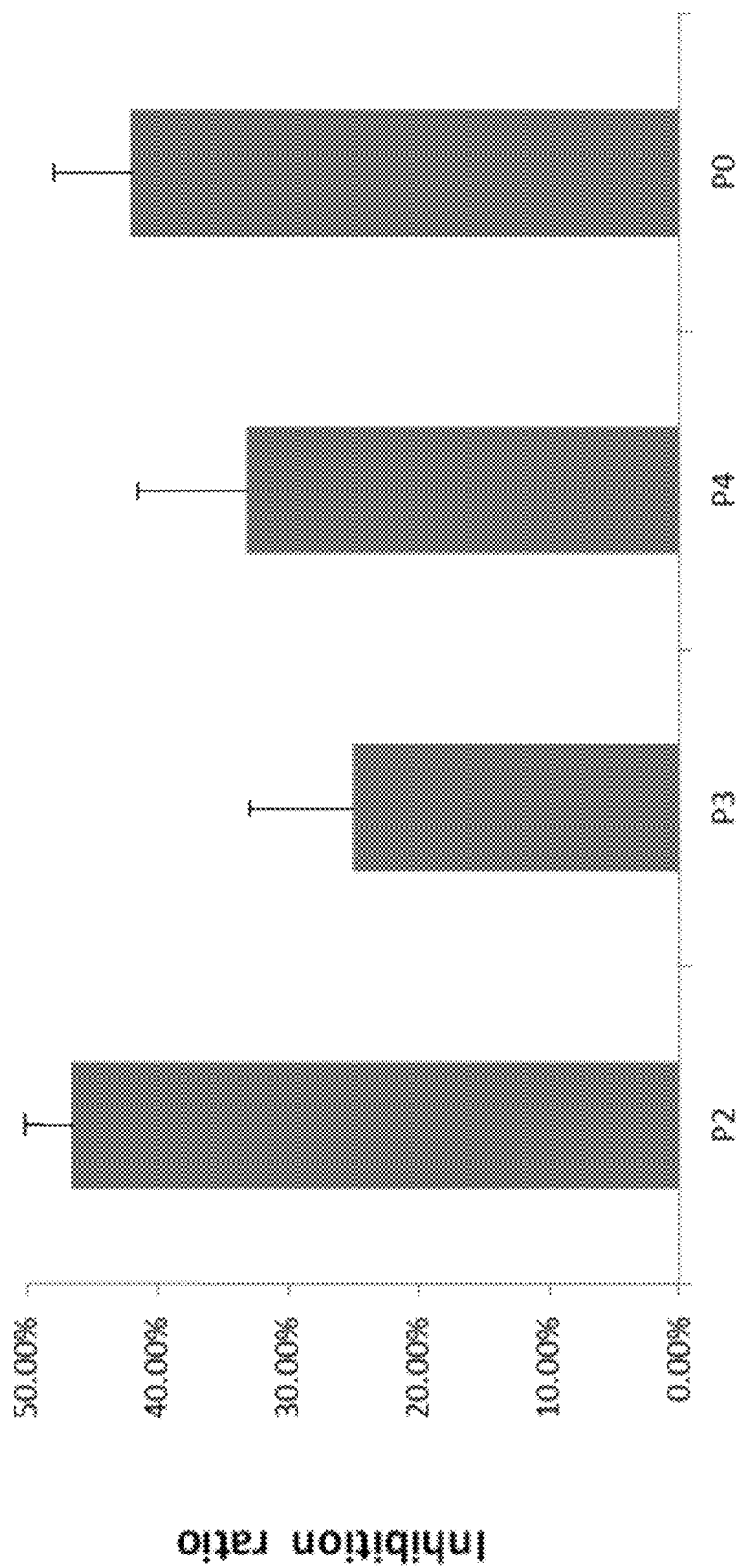

Target cells (i.e., NalM-6 expressing PD-L1 or NalM-6) and various effector cells (i.e., transduced T cells) or negative control cells (i.e., non-transduced T cells) were cultured for about 24 hours with a number ratio between the target cells and effector cells or negative control cells being about 10:1. IFN-gamma production of transduced T cells was measured. As shown in FIGS. 6A and 6B, IFN-gamma productions by CAR T cells were reduced, which indicated loss of cytotoxicity in response to expression of PD-L1 on NalM-6 cells. Further, as compared to CAT T cells without modified PD-1, loss of cytotoxicity induced by a PD-L1 decrease on CART cells transduced with modified PD-1. For example, loss of cytotoxicity of T cells transduced with CAR and PD-1 having a point mutation (i.e., P3) is about 22%, which is lower than 43% of CAR T cells without modified PD-1 (i.e., P0). This indicates that Inhibition of cytotoxicity induced by PD-L1 decreases on T cells transduced with CAR and modified PD-1. All error bars are representative of standard deviation.

Techniques related to cell cultures, construction of cytotoxic T-lymphocyte assay may be found in Chimeric Receptors Containing CD137 Signal Transduction Domains Mediate Enhanced Survival of T Cells and Increased Antileukemic Efficacy in Vivo Molecular Therapy vol. 17 no. 8, 1453-1464 August 2009, which is incorporated herein by reference.

EMBODIMENTS

Embodiment 1

An isolated nucleic acid sequence comprising a nucleic acid sequence that encodes modified programmed cell death protein 1 (PD-1) and a nucleic acid sequence that encodes chimeric antigen receptor (CAR), wherein the modified PD-1 and the CAR are expressed as gene products that are separate polypeptides.

Embodiment 2

The isolated nucleic acid sequence of embodiment 1, wherein the CAR is specific for a tumor antigen that is present on a cancer cell, and wherein the cancer cell or a cell associated with the cancer cell expresses PD-L1.

Embodiment 3

The isolated nucleic acid sequence of embodiment 2, wherein the tumor antigen comprises CD19.

Embodiment 4

The isolated nucleic acid sequence of embodiment 1, wherein the nucleic acid sequence that encodes the modified PD-1 comprises substitution or deletion of one or more nucleotides as compared to a nucleic acid sequence encoding an intracellular part of wild-type PD-1.

Embodiment 5

The isolated nucleic acid sequence of embodiment 1, wherein the nucleic acid sequence that encodes the modified PD-1 comprises a deletion of multiple nucleotides as compared to a nucleic acid sequence encoding an intracellular part of wild-type PD-1.

Embodiment 6

The isolated nucleic acid sequence of embodiment 5, wherein the modified PD-1 comprises the amino acid sequence of SEQ ID NO: 14.

Embodiment 7

The isolated nucleic acid sequence of embodiment 4, wherein the nucleic acid sequence that encodes the modified PD-1 comprises a nucleic acid encoding a truncated PD-1 that does not include an intracellular domain.

Embodiment 8

The isolated nucleic acid sequence of embodiment 7, wherein the nucleic acid sequence that encodes the modified PD-1 comprises the amino acid sequence of SEQ ID NO: 12.

Embodiment 9

The isolated nucleic acid sequence of embodiment 1, wherein the modified PD-1 comprises a point mutation as compared to wild-type PD-1.

Embodiment 10

The isolated nucleic acid sequence of embodiment 9, wherein the point mutation comprises one or two amino acid point mutations of phosphorylation sites of wild-type PD-1.

Embodiment 11

An expression vector comprising the isolated nucleic acid sequence of any of embodiment 1 to 10.

Embodiment 12

The expression vector of embodiment 11, wherein the expression vector is a viral vector selected from the group consisting of a retroviral vector, lentiviral vector, adenoviral vector, and an adeno-associated viral vector.

Embodiment 13

A cell comprising the expression vector of embodiment 11.

Embodiment 14

The cell embodiment 13, wherein the cell is selected from the group consisting of a T cell, NK cell, and an NKT cell.

Embodiment 15

A pharmaceutical composition comprising an antitumor effective amount of a population of human T cells, wherein the human T cells of the population include human T-cells that comprise the isolated nucleic acid sequence of any of embodiments 1 to 10.

Embodiment 16

The pharmaceutical composition of embodiment 15, wherein an inhibitory effect of PD-L1 on cytokine production of the human T cells of the population is less than an inhibitory effect of PD-L1 on cytokine production of human T cells that do not comprise at least a part of the nucleic acid sequence that encodes the modified PD-1.

Embodiment 17

A method of treating cancer in a human patient, the method comprising administering to the human patient the pharmaceutical composition of embodiment 16.

Embodiment 18

A cell engineered to express modified PD-1 and chimeric antigen receptors (CAR), wherein the modified PD-1 does not include a transmembrane part or an intracellular part of PD-1, or a combination thereof.

Embodiment 19

The cell of embodiment 18, wherein the cell expresses soluble PD-1 such as to disrupt PD-1 binding to PD-L-1.

Embodiment 20

The cell of embodiment 19, wherein the soluble PD-1 is not attached to a cell membrane of the cell.

Embodiment 21

A modified cell comprising: a receptor polypeptide, a cytoplasmic domain of the receptor polypeptide being truncated, the receptor polypeptide being at least one of a Programmed cell death protein 1 (PD-1) receptor polypeptide, cytotoxic T-lymphocyte-associated protein 4 (CTLA-4) receptor polypeptide, or B- and T-lymphocyte attenuator (BTLA) receptor.

Embodiment 22

A method for treating a subject having a disease, the method comprising: administering a cell to the subject having the disease, wherein the cell is genetically modified to express: a receptor polypeptide, a cytoplasmic domain of the receptor polypeptide being truncated, the receptor polypeptide being at least one of a Programmed cell death protein 1 (PD-1) receptor polypeptide, cytotoxic T-lymphocyte-associated protein 4 (CTLA-4) receptor polypeptide, or B- and T-lymphocyte attenuator (BTLA) receptor; and a chimeric antigen receptor (CAR) comprising an antigen recognition domain of a specific antibody and an intracellular domain or a modified or wild-type T cell receptor, the specific antibody binding to an antigen.

Embodiment 23

The modified cell or the method of embodiment 21 or 22, wherein the receptor polypeptide is the PD-1 receptor polypeptide, and wherein the cytoplasmic domain of the PD-1 receptor polypeptide contains an immunoreceptor tyrosine-based motif.

Embodiment 24

The modified cell or the method of embodiment 21 or 22, wherein the specific antibody binds to an antigen.

Embodiment 25

A modified cell comprising: a reduced amount of one or more receptors as compared to a corresponding wild-type cell, the one or more receptors comprising at least one of a Programmed cell death protein 1 (PD-1), cytotoxic T-lymphocyte-associated protein 4 (CTLA-4), or B- and T-lymphocyte attenuator (BTLA).

Embodiment 26

A method for treating a subject having a disease, the method comprising: administering a cell to the subject having the disease, wherein the cell is modified to express: a reduced amount of one or more receptors as compared to a corresponding wild-type cell, the one or more receptors comprising at least one of a Programmed cell death protein 1 (PD-1), cytotoxic T-lymphocyte-associated protein 4 (CTLA-4), or B- and T-lymphocyte attenuator (BTLA).

Embodiment 27

The modified cell of embodiments 21 or 25, wherein the modified cell further comprises a chimeric antigen receptor (CAR) comprising an antigen recognition domain of a specific antibody and an intracellular domain, or a modified or wild-type T cell receptor.

Embodiment 28

The method of embodiments 22 or 26, wherein the modified cell further comprises a chimeric antigen receptor (CAR) comprising an antigen recognition domain of a specific antibody and an intracellular domain or a modified or wild-type T cell receptor, the specific antibody binding to an antigen.

Embodiment 29

The modified cell or the method of embodiments 25 or 26, wherein the modified cell has reduced expression of one or more genes associated with a biosynthesis pathway or transportation pathway of the one or more receptors as compared to the corresponding wild-type cell, or a combination thereof.

Embodiment 30

The modified cell or the method of embodiments 25 or 26, wherein the modified cell comprises a disruption of the one or more genes.

Embodiment 31

The modified cell or the method of embodiments 25 or 26, wherein the modified cell comprises a partial or a complete deletion of the PD-1 gene.

Embodiment 32

The method of embodiments 22 or 26, wherein the genetically modified cell replicate in vivo in the human patient.

Embodiment 33

The method of embodiments 22 or 26, wherein the modified cell from memory cells in the human patient.

Embodiment 34

The method of embodiments 22 or 26, wherein the modified cells are administered intravenously to the human patient.

Embodiment 35

The method of embodiments 22 or 26, wherein the modified cells persist in the human patient.

Embodiment 36

The method of embodiments 32, wherein the modified cell is an autologous T cell.

Embodiment 37

The modified cell or the method of embodiments 21, 22, 25 or 26, wherein the cell comprises at least one of a B cell, a T cell, an NK cell, an embryonic cell, or a dendritic cell.

Embodiment 38

The method of any of embodiments 22 or 26, wherein the disease comprises at least one of cancer, immune deficiencies, autoimmune disease, or obesity.

Embodiment 39

A method of treating and/or inhibiting cancer of a subject, the method comprising administering to the subject a therapeutically effective amount of a soluble receptor comprising an extracellular domain of PD-1.

Embodiment 40

The method of embodiment 39, wherein the soluble receptor binds a PD-L1 protein, and the soluble receptor disrupts PD-1 signaling of cancer cells and/or disrupts PD-1 binding to PD-L1.

Embodiment 41

The method of embodiment 39, wherein the soluble receptor polypeptide includes the amino acid residues of SEQ ID NO:9.

What is claimed is:

1. A pharmaceutical composition comprising human T cells, wherein the human T cells comprising:
   a first nucleic acid sequence that encodes a modified programmed cell death protein 1 (PD-1) that reduces an inhibitory effect of programmed death ligand 1 (PD-L1) on the human T cells, the modified PD-1 lacking a functional PD-1 intracellular domain for PD-1 signal transduction, wherein the modified PD-1 is a soluble receptor or comprises a mutation at amino acid 223 and/or 248; and
   a second nucleic acid sequence that encodes a chimeric antigen receptor (CAR) comprising an extracellular domain that recognizes a tumor antigen of a target cell, a transmembrane domain, and an intracellular domain comprising a CD3-zeta signaling domain and a signaling domain of a costimulatory molecule; and
   wherein the modified PD-1 and the CAR are expressed as gene products that are separate polypeptides.

2. The pharmaceutical composition of claim 1, wherein the modified PD-1 interferes with a pathway between PD-1 of a human T cell of the human cells and PD-L1 of a certain cell.

3. The pharmaceutical composition of claim 1, wherein the modified PD-1 comprises a PD-1 extracellular domain.

4. The pharmaceutical composition of claim 1, wherein the modified PD-1 comprises:
   a modified PD-1 intracellular domain comprising a substitution at amino acid 223 and/or 224; and
   the amino acid sequence of SEQ ID NO: 9 or the amino acid sequence of SEQ ID NO: 10, or a combination thereof.

5. The pharmaceutical composition of claim 1, wherein the modified PD-1 is a soluble receptor comprising a PD-1 extracellular domain that binds to PD-L1 of a certain cell.

6. The pharmaceutical composition of claim 1, wherein the tumor antigen is CD19.

7. The pharmaceutical composition of claim 1, wherein the costimulatory molecule comprises 4-1BB or CD28, or a combination thereof.

8. The pharmaceutical composition of claim 3, wherein an intracellular domain of the modified PD-1 comprises the amino acid sequence of SEQ ID NO: 12.

9. The pharmaceutical composition of claim 3, wherein an intracellular domain of the modified PD-1 comprises the amino acid sequence of SEQ ID NO: 13.

10. The pharmaceutical composition of claim 3, wherein an intracellular domain of the modified PD-1 comprises the amino acid sequence of SEQ ID NO: 14.

11. A method of reducing an inhibitory effect of PD-L1 on human T cells, the method comprising:
    introducing a first nucleic acid sequence and a second nucleic acid sequence into the human T cells, wherein:
    a first nucleic acid sequence encodes a modified PD-1 that reduces the inhibitory effect of PD-L1 on the human T cells, the modified PD-1 lacking a functional PD-1 intracellular domain for PD-1 signal transduction, wherein the modified PD-1 is a soluble receptor or comprises a mutation at amino acid 223 and/or 248; and
    a second nucleic acid sequence encodes a CAR comprising an extracellular domain that recognizes a tumor antigen of a target cell, a transmembrane domain, and an intracellular domain comprising a CD3-zeta signaling domain and a signaling domain of a costimulatory molecule;
    and wherein the modified PD-1 and the CAR are expressed as gene products that are separate.

12. The method of claim 11, wherein the modified PD-1 interferes with a pathway between PD-1 of a human T cell of the human cells and PD-L1 of a certain cell.

13. The method of claim 11, wherein the modified PD-1 comprises a PD-1 extracellular domain.

14. The method of claim 11, wherein the modified PD-1 comprises:
    a modified PD-1 intracellular domain comprising a substitution at amino acid 223 and/or 224; and
    the amino acid sequence of SEQ ID NO: 9 or the amino acid sequence of SEQ ID NO: 10, or a combination thereof.

15. The method of claim 11, wherein the modified PD-1 is a soluble receptor comprising a PD-1 extracellular domain that binds to PD-L1 of a certain cell.

16. The method of claim 11, wherein the tumor antigen is CD19.

17. The method of claim 11, wherein the costimulatory molecule comprises 4-1 BB or CD28, or a combination thereof.

18. The method of claim 13, wherein an intracellular domain of the modified PD-1 comprises the amino acid sequence of SEQ ID NO: 12.

19. The method of claim 13, wherein an intracellular domain of the modified PD-1 comprises the amino acid sequence of SEQ ID NO: 13.

20. The method of claim 13, wherein an intracellular domain of the modified PD-1 comprises the amino acid sequence of SEQ ID NO: 14.

21. The pharmaceutical composition of claim 1, wherein the first nucleic acid sequence comprises SEQ ID NO: 4.

22. The method of claim 11, wherein the first nucleic acid sequence comprises sequence of SEQ ID NO: 4.

23. The method of claim 11, wherein the modified PD-1 comprises a truncated PD-1 that does not include an intracellular domain.

24. The pharmaceutical composition of claim 1, wherein the PD-1 is a soluble receptor.

25. The pharmaceutical composition of claim 1, wherein the PD-1 comprises a mutation at amino acid 223 and/or 248.

26. The method of claim 11, wherein the PD-1 is a soluble receptor.

27. The method of claim 11, wherein the PD-1 comprises a mutation at amino acid 223 and/or 248.

* * * * *